United States Patent
Park et al.

(10) Patent No.: US 8,946,283 B2
(45) Date of Patent: Feb. 3, 2015

(54) COMPOSITION FOR PREVENTING OR TREATING OBESITY, DYSLIPIDEMIA, FATTY LIVER OR DIABETES CONTAINING INDOLE-3-CARBINOL DERIVATIVE AS ACTIVE INGREDIENT

(75) Inventors: Tae Sun Park, Seoul (KR); Gyoon Hee Han, Hwaseong-si (KR)

(73) Assignees: Industry-Academic Cooperation Foundation, Yonsei University, Seoul (KR); Korea Health Industry Development Institute (KHIDI), Chungcheongbuk-do (KR)

( * ) Notice: Subject to any disclaimer, the term of this patent is extended or adjusted under 35 U.S.C. 154(b) by 0 days.

(21) Appl. No.: 13/983,711

(22) PCT Filed: Dec. 27, 2011

(86) PCT No.: PCT/KR2011/010161
§ 371 (c)(1),
(2), (4) Date: Aug. 5, 2013

(87) PCT Pub. No.: WO2012/108622
PCT Pub. Date: Aug. 16, 2012

(65) Prior Publication Data
US 2013/0317077 A1 Nov. 28, 2013

(30) Foreign Application Priority Data

Feb. 7, 2011 (KR) ........................ 10-2011-0010585

(51) Int. Cl.
| | |
|---|---|
| A01N 43/38 | (2006.01) |
| A61K 31/40 | (2006.01) |
| C07D 409/14 | (2006.01) |
| A61K 31/404 | (2006.01) |
| C07D 209/38 | (2006.01) |
| C07D 403/04 | (2006.01) |

(52) U.S. Cl.
CPC ............ *C07D 409/14* (2013.01); *A61K 31/404* (2013.01); *C07D 209/38* (2013.01); *C07D 403/04* (2013.01)
USPC ........................................................ 514/414

(58) Field of Classification Search
None
See application file for complete search history.

(56) References Cited

U.S. PATENT DOCUMENTS

| | | |
|---|---|---|
| 2008/0188472 A1 | 8/2008 | Bradley et al. |
| 2009/0258876 A1 | 10/2009 | Seong et al. |

OTHER PUBLICATIONS (Obesity Prevention, Mayo Clinic Staff, retrieved from the internet Jun. 10, 2014).*
Rad-Moghadamn et al., Tetrahedron, 2010, 66, 2316-2321.*
Chauhan et al., Chem. Eur. J., 2010, 16, 7709-7713.*
Chauhan et al., "Asymmetric addition of indoles to isatins catalysed by bifunctional modified cinchona alkaloid catalysts," Chemistry. 16(26):7709-13 (2010).
Rad-Moghadam et al., "Synthesis of symmetrical and unsymmetrical 3,3-di(indolyl)indolin-2-ones under controlled catalysis of ionic liquids," Tetrahedron. 66(13):2316-2321 (2010).
International Search Report for International Application No. PCT/KR2011/010161, mailed Jun. 26, 2012 (4 pages).

* cited by examiner

*Primary Examiner* — Dennis Heyer
*Assistant Examiner* — Daniel M Podgorski
(74) *Attorney, Agent, or Firm* — Clark & Elbing LLP

(57) ABSTRACT

Disclosed is a composition for preventing or treating obesity, dyslipidemia, fatty liver or diabetes, containing an indole-3-carbinol derivative as an active ingredient. The indole-3-carbinol derivative of the present disclosure can be usefully used as a pharmaceutical or functional food composition for preventing or treating obesity, dyslipidemia, fatty liver or diabetes by inhibiting differentiation of preadipocytes and reducing accumulation of triglyceride in cells.

7 Claims, 14 Drawing Sheets

COMPOSITION FOR PREVENTING OR TREATING OBESITY, DYSLIPIDEMIA, FATTY LIVER OR DIABETES CONTAINING INDOLE-3-CARBINOL DERIVATIVE AS ACTIVE INGREDIENT

CROSS-REFERENCE TO RELATED APPLICATIONS

This application is the U.S. national stage filing under 35 U.S.C. §371 of PCT International Application PCT/KR2011/010161, filed Dec. 27, 2011, which claims priority from Korean Patent Application 10-2011-0010585, filed Feb. 7, 2011.

TECHNICAL FIELD

The present disclosure relates to a composition for preventing or treating obesity, dyslipidemia, fatty liver or diabetes containing indole-3-carbinol derivative as an active ingredient.

BACKGROUND ART

As abdominal obesity increases in modern people with the change in lifestyles, occurrence of metabolic syndromes including diabetes, hypertension, dyslipidemia, insulin resistance, etc. is increasing rapidly. These diseases increase the risk of incidence one another and are commonly related to the cause of metabolic changes, such as aging, stress and suppressed immune system. Obesity is considered unattractive and causes such chronic diseases as fatty liver, hypertension, diabetes, cardiovascular diseases, or the like. According to the 2007 Korea National Health and Nutrition Examination Survey recently reported by the Ministry of Health & Welfare, 31.7% of Korean adults turned out to be obese, meaning that 3 out of 10 Korean adults are exposed to obesity-related complications. The increase in overweight and obese population leads to increased prevalence of chronic diseases. The number of diabetic patients in Korea is expected to increase from 3,000,000 in 2007 to 5,450,000 in 2030, meaning that 10% of Koreans will be diabetic patients. In 2005, deaths caused by diabetes in Korea were 35.5 per 100,000 people, 3-7 times more than those of Japan (5.9), England (7.5) or Germany (16.6). According to the Korea Institute for Health and Social Affairs, the socioeconomic loss caused by obesity and obesity-related complications in 2006 is estimated at 2.1 trillion won including medical cost and indirect cost such as loss of earning. Thus, in 2010, the Korean government has decided to reduce the obesity rate down to 20% in adults and to 15% in youth, and is exploring ways to accurately define and diagnose obesity and metabolic diseases.

At present, 1.7 billion people amounting to about 25% of the world population are overweight (BMI >25) and more than 300 million people including 120 million in the US, Europe and Japan are classified as obese (BMI >30). Among the OECD countries, the US has the highest obesity rate of 31% of population, followed by Mexico (24%), England (23%), Greece (22%), Australia (22%), New Zeeland (21%), Hungary (19%), Canada (14%), Spain (13%), Ireland (13%), Germany (13%), Portugal (13%), Finland (13%), Turkey (12%) and Belgium (12%). The number of obese people in China is 70 million and the body weight control-related market is expanding, estimated at about 10 billion yuan. Childhood obesity is also increasing rapidly worldwide, with 1 in 5 children being obese. As such, childhood obesity is becoming a serious social issue. Since childhood obesity is the main cause of the life style diseases including diabetes, hypertension, stroke, etc. with increased blood cholesterol and triglyceride level, 80% or more of obese children are likely to become obese adults. Further, since increased fat stimulates secretion of sex hormones and induces early adolescence, childhood obesity may cause growth problems. Also, it negatively affects blood circulation and nourishment.

Obesity drugs that are marketed inside and outside Korea include 'Xenical' (Roche Korea) with orlistat as main ingredient and approved by the FDA, 'Reductil' (Ilsung Pharmaceuticals) with sibutramine as main ingredient, 'Exolise' (Guju Pharma) with green tea catechol as main ingredient, or the like. Xenical, which reduces absorption of fat by inhibiting lipase, has the gastrointestinal-related side effects such as steatorrhea, gas generation and reduced absorption of oil-soluble vitamins. Reductil, which increases serotonin and noradrenaline levels in the sympathetic nervous system, has side effects such as headache, dry mouth, loss of appetite, insomnia, constipation, etc. Besides, a large number of anti-obesity drugs have been withdrawn from the market due to severe side effects. For example, aminophylline is reported to have various side effects in the nervous, circulatory and digestive systems despite its excellent effect of reducing body fat. Also, fenfluramine, dexfenfluramine, topiramate, ephedrine, etc. have been banned from being marketed as obesity drugs. As the synthetic drugs show limitations in side effects and in overcoming chronic diseases, foods and drugs derived from natural sources are drawing attentions.

The inventors of the present disclosure have found out that the phytochemical indole-3-carbinol contained in large quantities in the *Brassica* plants such as broccoli, cabbage, etc. has the activity of inhibiting obesity. Indole-3-carbinol has a molecular formula of $C_9H_9NO$ and a molecular weight of 147.17.

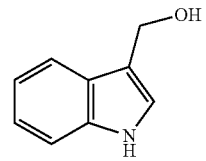 [SMILES: OCc1c[nH]c2ccccc12]

Indole-3-carbinol is a greyish or white solid and is produced during cutting, trituration or mastication or by enzymes in organisms. It is produced by the enzyme myrosinase from its precursor indole-3-glucosinolate.

Throughout the specification, a number of publications and patent documents are referred to and cited. The disclosure of the cited publications and patent documents is incorporated herein by reference in its entirety to more clearly describe the state of the related art and the present disclosure.

DISCLOSURE

Technical Problem

The inventors of the present disclosure have found out that the natural substance indole-3-carbinol extracted from cruciferous vegetables has anti-obesity, anti-hyperlipidemic and/or anti-diabetic activities and have studied to further explore various derivatives of indole-3-carbinol having comparable or better activities as compared to indole-3-carbinol based on the previous finding. As a result, they have found out that an indole-3-carbinol derivative represented by Chemical Formula 1 or Chemical Formula 2 has superior activity of inhibiting adipocyte differentiation.

The present disclosure is directed to providing a composition for preventing or treating obesity, dyslipidemia, fatty liver or diabetes, containing an indole-3-carbinol derivative as an active ingredient.

The present disclosure is also directed to providing a food composition for preventing or improving obesity, dyslipidemia, fatty liver or diabetes, containing an indole-3-carbinol derivative as an active ingredient.

Other features and aspects will be apparent from the following detailed description, drawings and claims.

Technical Solution

In one general aspect, the present disclosure provides a composition for preventing or treating obesity, dyslipidemia, fatty liver or diabetes, containing an indole-3-carbinol derivative represented by Chemical Formula 1 or Chemical Formula 2 as an active ingredient:

Chemical Formula 1

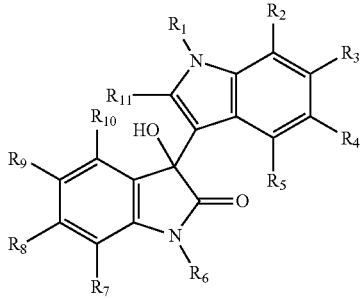

wherein $R_1$ is hydrogen or $C_1$-$C_4$ alkyl, $R_2$-$R_5$ are hydrogen, $R_7$-$R_{10}$ are independently hydrogen or halo, $R_6$ is $C_1$-$C_4$ alkyl, $C_2$-$C_6$ alkenyl, phenyl $C_1$-$C_4$ alkyl, 5- or 6-membered heteroaryl $C_1$-$C_4$ alkyl, phenoxy $C_1$-$C_4$ alkyl or $C_1$-$C_4$ alkoxyphenoxy $C_1$-$C_4$ alkyl, and $R_{11}$ is hydrogen or methyl; and Chemical Formula 2

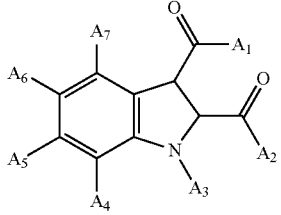

wherein $A_1$ and $A_2$ are independently $C_1$-$C_4$ alkyl or hydroxy, $A_3$ is hydrogen or $C_1$-$C_4$ alkyl, and $A_4$-$A_7$ are independently hydrogen or $C_1$-$C_4$ alkyl.

In another general aspect, the present disclosure provides a food composition for preventing or improving obesity, dyslipidemia, fatty liver or diabetes, containing the indole-3-carbinol derivative represented by Chemical Formula 1 or Chemical Formula 2 as an active ingredient.

Advantageous Effects

The features and advantages of the present disclosure can be summarized as follows:

(a) The present disclosure provides a pharmaceutical composition or functional food composition for preventing or treating obesity, dyslipidemia, fatty liver or diabetes, containing an indole-3-carbinol derivative as an active ingredient.

(b) The indole-3-carbinol derivative of the present disclosure can be usefully used as a pharmaceutical or functional food composition for preventing or treating obesity, dyslipidemia, fatty liver or diabetes by inhibiting differentiation of preadipocytes and reducing accumulation of triglyceride in cells.

Figure 10:
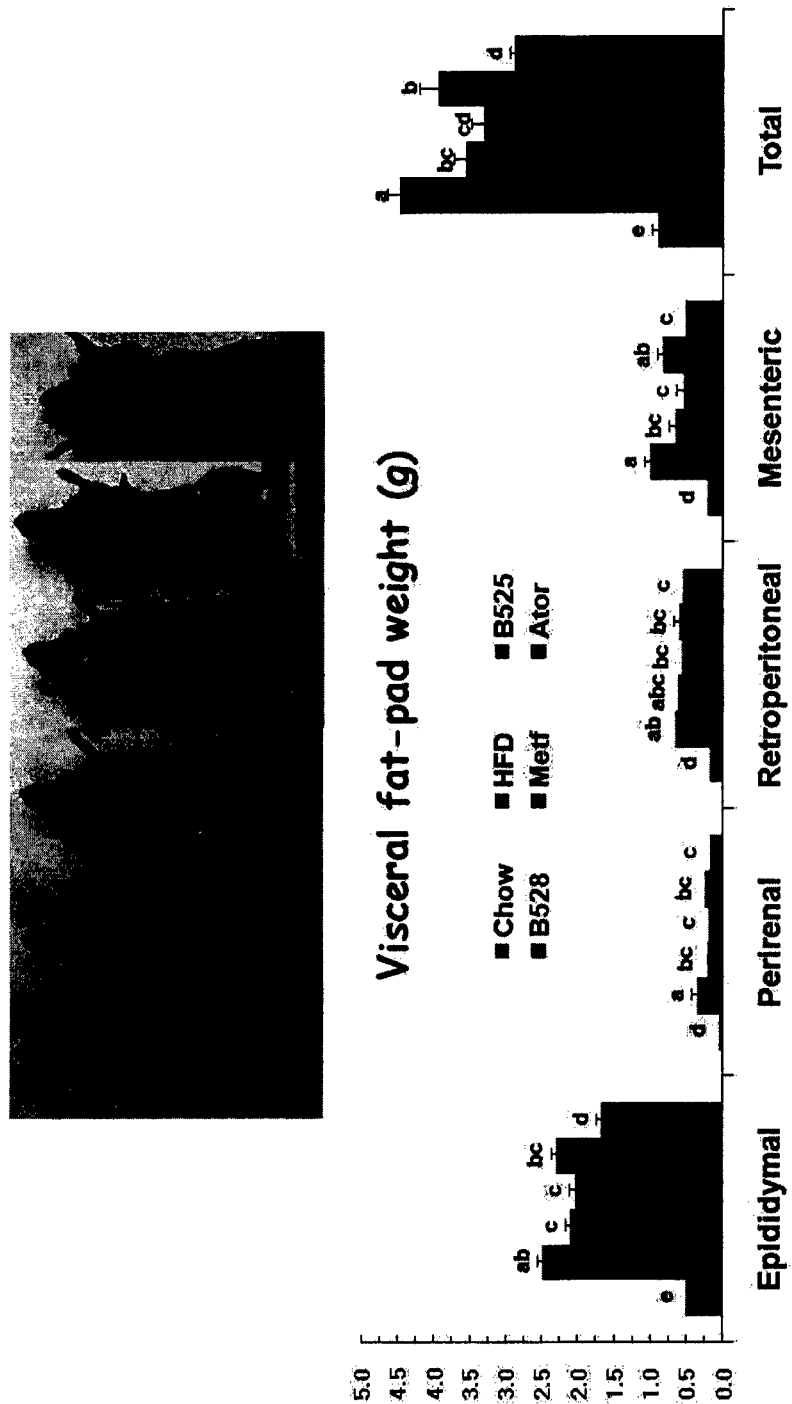

FIG. 10 shows visceral fat weight of mice fed with test diet. The result is represented as mean±SEM of 8 mice. The characters above the bars indicate significant difference by one-way ANOVA test (P<0.001).

Figure 11:
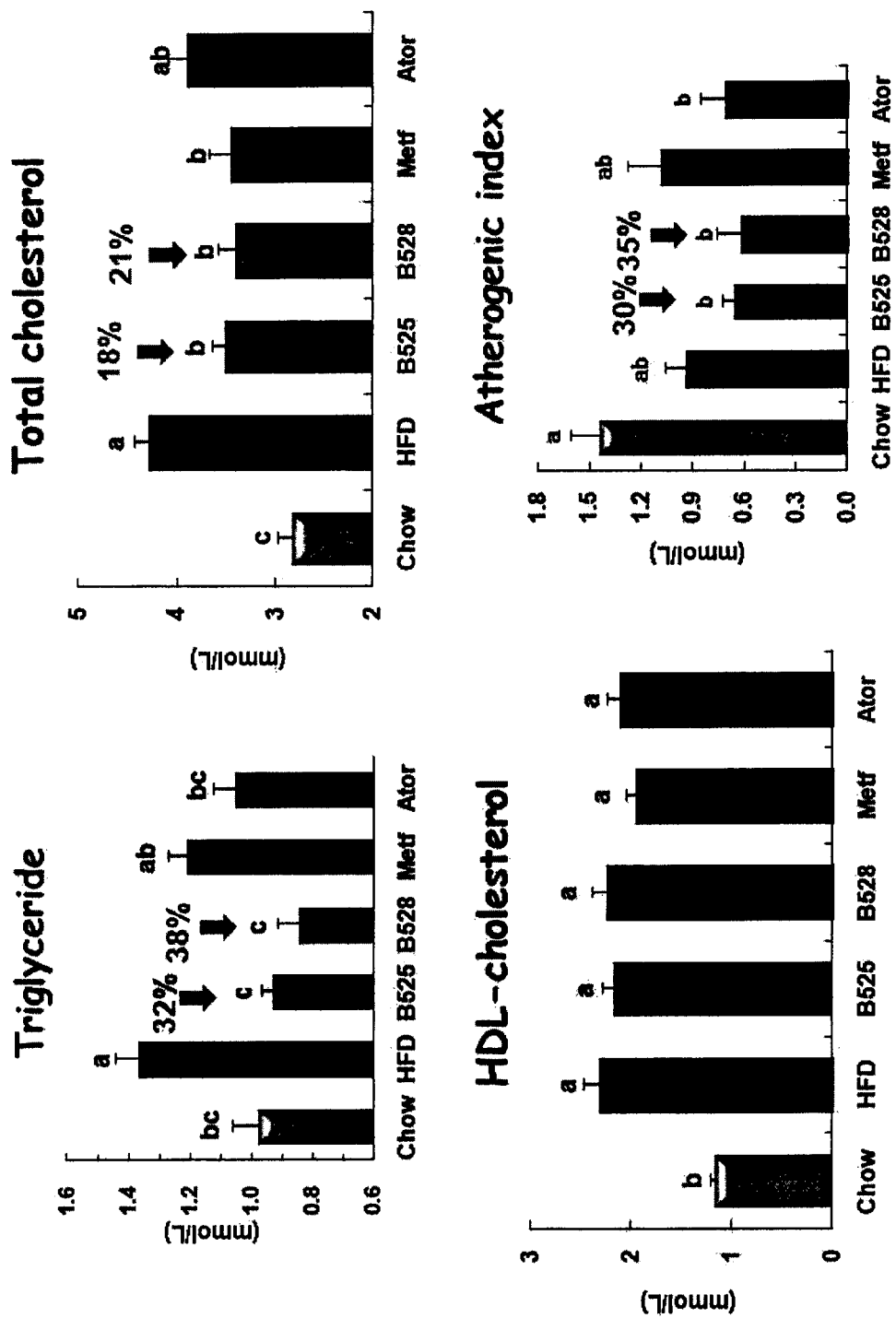

FIG. 11 shows blood lipid level of mice fed with test diet. The result is represented as mean±SEM of 8 mice. The characters above the bars indicate significant difference by one-way ANOVA test (P<0.05).

Figure 12:
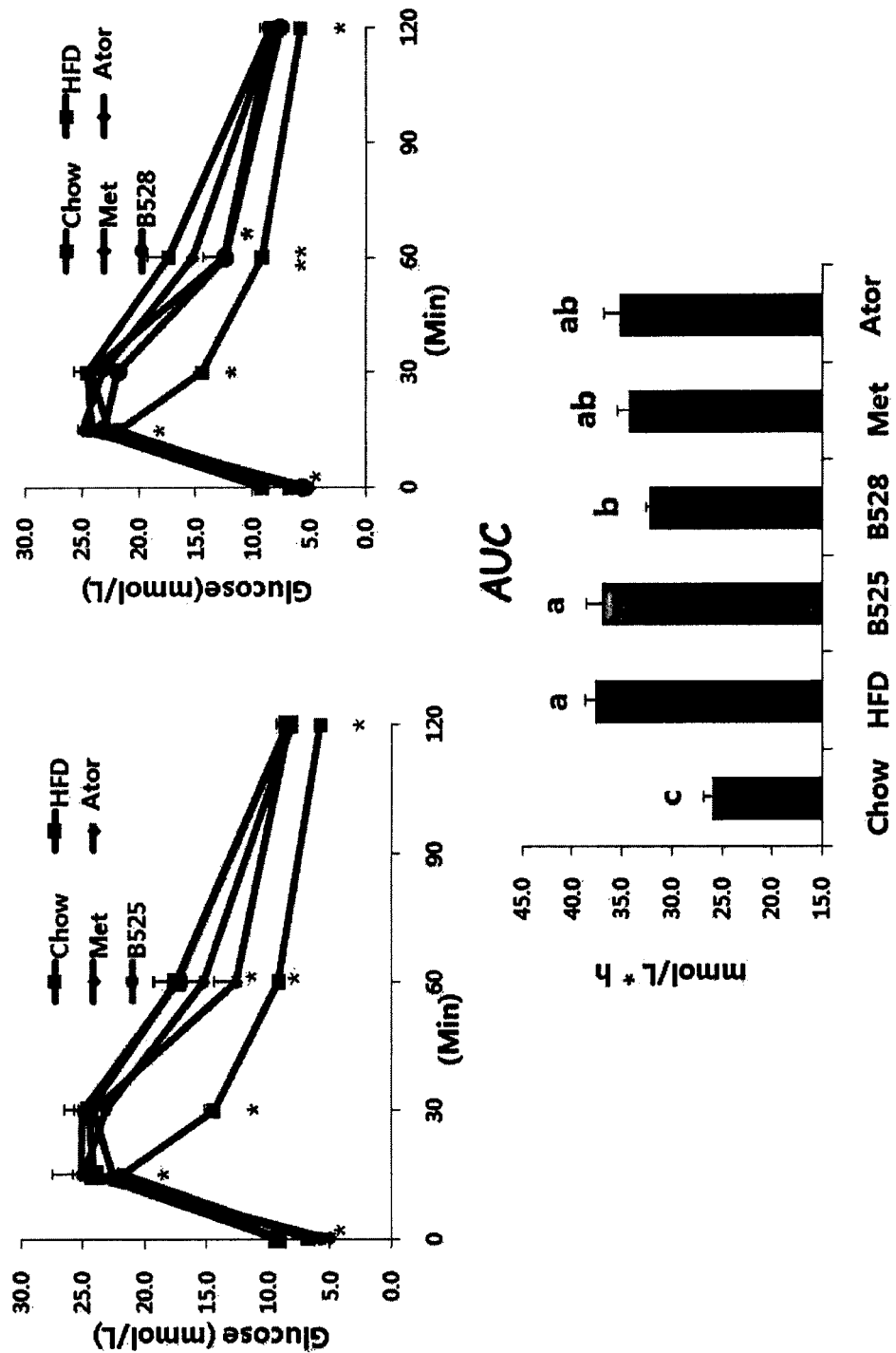

FIG. 12 shows a result of oral glucose tolerance test for mice fed with test diet. The result is represented as mean±SEM of 8 mice. The characters above the bars indicate significant difference by one-way ANOVA test (P<0.05).

Figure 13:
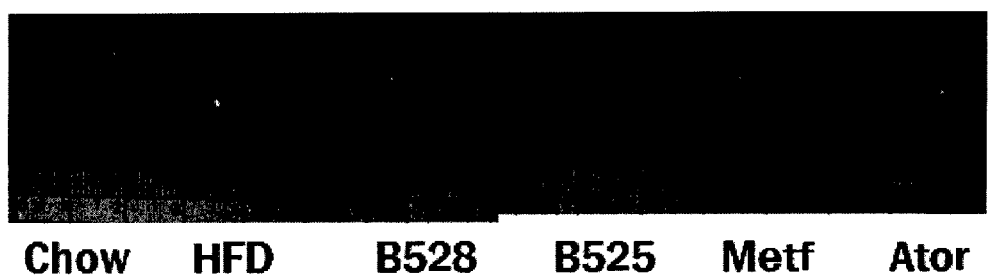
Figure 13:
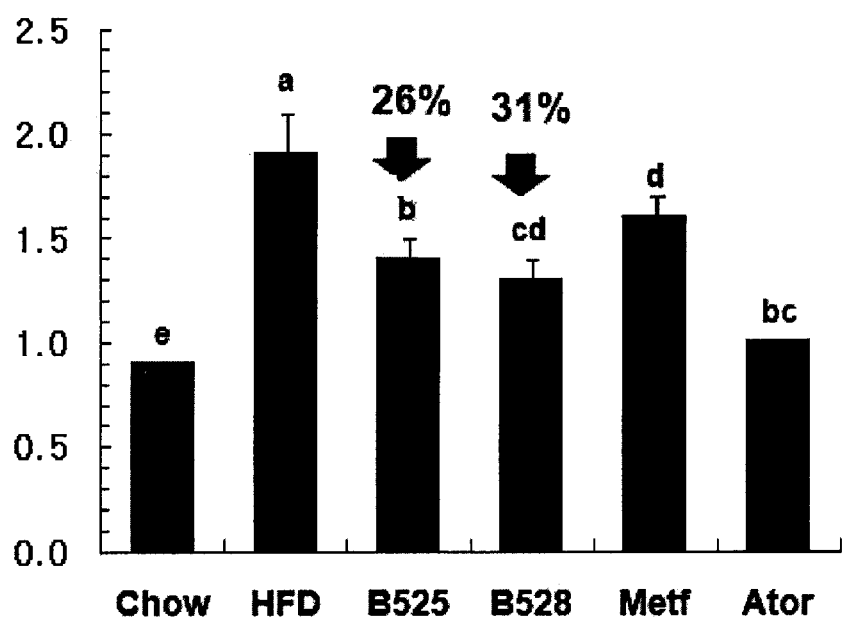

FIG. 13 shows images of mouse liver tissue as well as liver weight. The result is represented as mean±SEM of 8 mice. The characters above the bars indicate significant difference by one-way ANOVA test (P<0.05).

Figure 14:
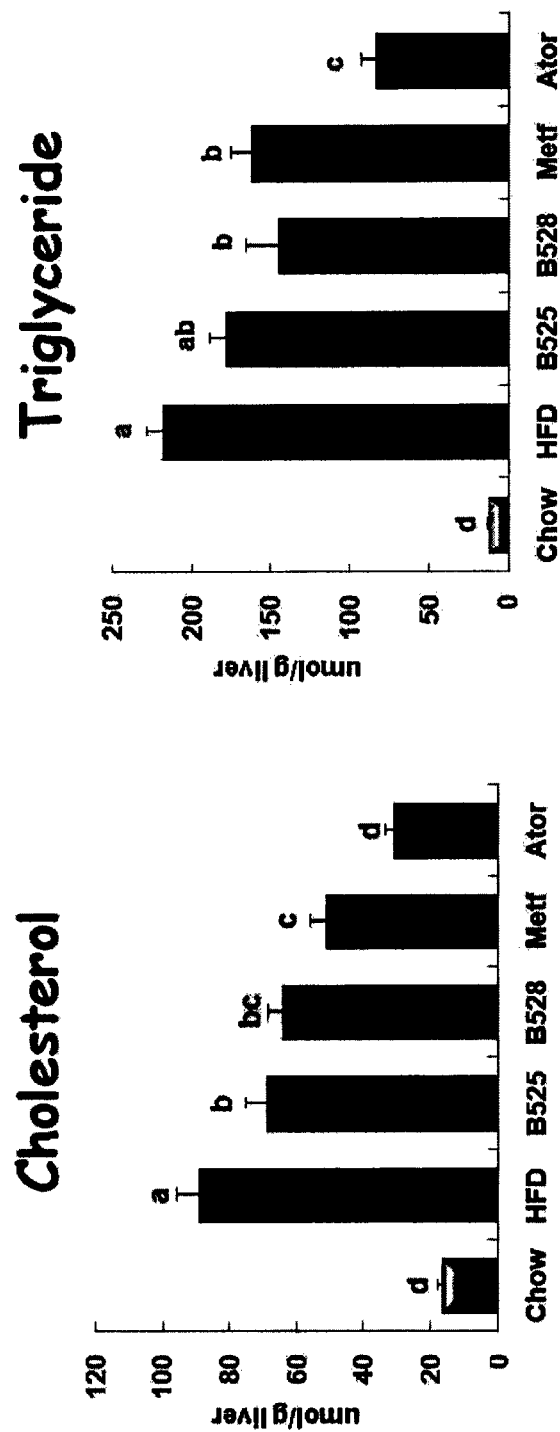

FIG. 14 shows lipid level in mouse liver tissue. The result is represented as mean±SEM of 8 mice. The characters above the bars indicate significant difference by one-way ANOVA test (P<0.05).

BEST MODE

Hereinafter, the embodiments of the present disclosure will be described in detail with reference to accompanying drawings.

The present disclosure provides a composition for preventing or treating obesity, dyslipidemia, fatty liver or diabetes, comprising an indole-3-carbinol derivative represented by Chemical Formula 1 or Chemical Formula 2 as an active ingredient:

Chemical Formula 1

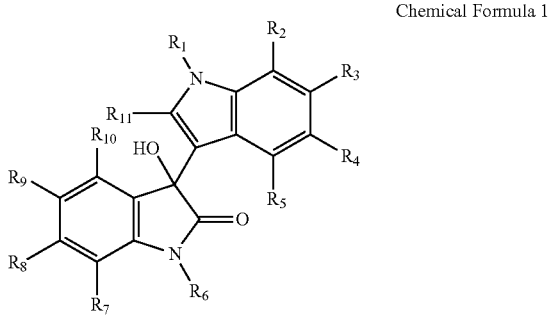

In the above chemical formula, $R_1$ is hydrogen or $C_1$-$C_4$ alkyl, $R_2$-$R_5$ are hydrogen, $R_7$-$R_{10}$ are independently hydrogen or halo, $R_6$ is $C_1$-$C_4$ alkyl, $C_2$-$C_6$ alkenyl, phenyl $C_1$-$C_4$ alkyl, 5- or 6-membered heteroaryl $C_1$-$C_4$ alkyl, phenoxy $C_1$-$C_4$ alkyl or $C_1$-$C_4$ alkoxyphenoxy $C_1$-$C_4$ alkyl, and $R_{11}$ is hydrogen or methyl.

Chemical Formula 2

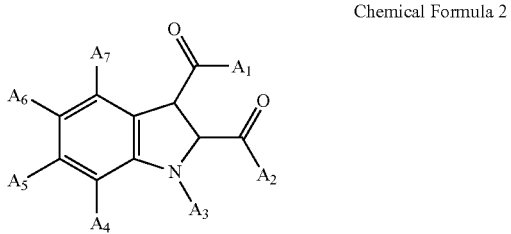

In the above chemical formula, $A_1$ and $A_2$ are independently $C_1$-$C_4$ alkyl or hydroxy, $A_3$ is hydrogen or $C_1$-$C_4$ alkyl, and $A_4$-$A_7$ are independently hydrogen or $C_1$-$C_4$ alkyl.

The inventors of the present disclosure have found out that the natural substance indole-3-carbinol extracted from cruciferous vegetables has anti-obesity, anti-hyperlipidemic and/or anti-diabetic activities and have studied to further explore various derivatives of indole-3-carbinol having comparable or better activities as compared to indole-3-carbinol based on the previous finding. As a result, they have found out that an indole-3-carbinol derivative represented by Chemical Formula 1 or Chemical Formula 2 has superior activity of inhibiting adipocyte differentiation.

The indole-3-carbinol derivative of the present disclosure represented by Chemical Formula 1 or Chemical Formula 2 inhibits differentiation of preadipocytes and reduces accumulation of triglyceride in cells in a concentration-dependent manner.

As used herein, the term "dyslipidemia" refers to an abnormal amount of lipids in the blood, including hyperlipidemia, hypercholesterolemia, hypertriglyceridemia, hypoalphalipoproteinemia and disorder of lipoprotein metabolism.

As used herein, the term "fatty liver" refers to a condition where fat accumulates excessively in liver cells due to the disorder of lipid metabolism. It may cause various diseases such as angina, myocardial infarction, stroke, arteriosclerosis and pancreatitis.

As used herein, the term "diabetes" refers to a chronic disease characterized by relative or absolute lack of insulin, leading to glucose intolerance. As used herein, the term diabetes includes all kinds of diabetes, such as type 1 diabetes, type 2 diabetes and genetic diabetes. Type 1 diabetes, which is insulin-dependent diabetes, mainly results from the destruction of β-cells. Type 2 diabetes, which is non-insulin-dependent diabetes, is caused by insufficient secretion of insulin after meals or by insulin resistance.

As used herein, the term "alkyl" refers to a saturated, substituted or unsubstituted hydrocarbon radical, which may be straight, branched or cyclic. For example, it includes methyl, ethyl, propyl, isobutyl, pentyl, hexyl, heptyl, octyl, nonyl, decyl, undecyl, tridecyl, pentadecyl, heptadecyl, cyclopropyl, cyclobutyl, cyclopentyl, etc. $C_1$-$C_4$ alkyl means an alkyl group having an alkyl unit of 1-4 carbon atoms. When the $C_1$-$C_4$ alkyl is substituted, the number of carbons in the substituent is not included.

As used herein, the term "halo" refers to a halogen element. For example, it includes fluoro, chloro, bromo and iodo.

As used herein, the term "alkenyl" refers to an unsaturated, substituted or unsubstituted hydrocarbon radical having a specified number of carbons, which may be straight or branched. For example, it includes ethenyl, vinyl, propenyl, allyl, isopropenyl, butenyl, isobutenyl, t-butenyl, n-pentenyl and n-hexenyl. In Chemical Formula 1, the $C_2$-$C_6$ alkenyl at the $R_6$ position means an alkenyl group having an alkenyl unit of 2-6 carbon atoms. When the $C_2$-$C_6$ alkenyl is substituted, the number of carbons in the substituent is not included.

As used herein, the term "aryl" refers to a wholly or partially unsaturated, aromatic, substituted or unsubstituted monocyclic or polycyclic ring.

As used herein, the term "heteroaryl" refers to a heterocyclic aromatic group containing a heteroatom such as oxygen, sulfur or nitrogen in the ring. Specifically, the heteroatom may be sulfur. The number of the heteroatoms may be 1-4, specifically 1-2. Specifically, the heteroaryl may be monoaryl or biaryl. The heteroaryl may have substituents at various positions. For example, it may be substituted with halo, hydroxy, nitro, cyano, $C_1$-$C_4$ substituted or unsubstituted straight or branched alkyl, or $C_1$-$C_4$ straight or branched alkoxy.

As used herein, the term "arylalkyl" refers to an alkyl group substituted with aryl. In Chemical Formula 1, the aryl $C_1$-$C_4$ alkyl at the $R_6$ position means an alkyl group having an alkyl unit of 1-4 carbon atoms substituted with aryl.

As used herein, the term "heteroarylalkyl" refers to an alkyl group substituted with heteroaryl. In Chemical Formula 1, the heteroaryl $C_1$-$C_4$ alkyl at the $R_6$ position means an alkyl group having an alkyl unit of 1-4 carbon atoms substituted with heteroaryl.

As used herein, the term "alkoxy" refers to a radical formed as hydrogen is removed from an alcohol group.

As used herein, the term "alkoxyalkyl" refers to an alkyl group substituted with alkoxy.

As used herein, the term "alkoxyalkoxyalkyl" refers to an alkyl group substituted with alkoxyalkoxy.

In an exemplary embodiment of the present disclosure, $R_1$ in Chemical Formula 1 is hydrogen.

In an exemplary embodiment of the present disclosure, $R_2$-$R_5$ and $R_7$-$R_{10}$ in Chemical Formula 1 are independently hydrogen, chlorine or bromine.

In an exemplary embodiment of the present disclosure, the heteroaryl of $R_6$ in Chemical Formula 1 is thiophene, furan, pyrrole or pyridine. More specifically, the heteroaryl may be thiophene.

In an exemplary embodiment of the present disclosure, $A_1$ in Chemical Formula 2 is hydroxy.

In an exemplary embodiment of the present disclosure, $A_2$ in Chemical Formula 2 is $C_1$-$C_4$ alkyl.

In an exemplary embodiment of the present disclosure, $A_4$-$A_7$ in Chemical Formula 2 are hydrogen.

In an exemplary embodiment of the present disclosure, the indole-3-carbinol derivative of the present disclosure represented by Chemical Formula 1 is selected from a group consisting of the compounds represented by Chemical Formulae 3-17:

Chemical Formula 3

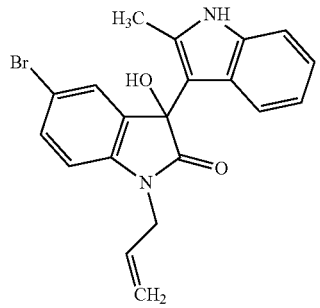

Chemical Formula 4

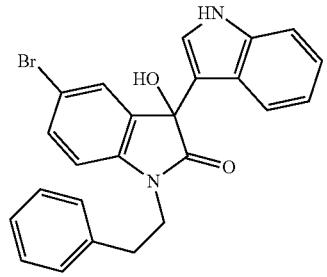

Chemical Formula 5

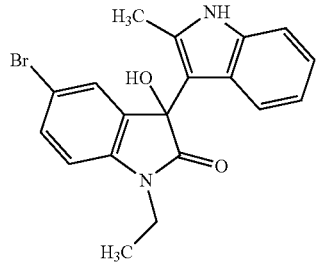

Chemical Formula 6

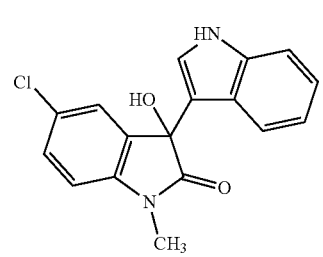

Chemical Formula 7

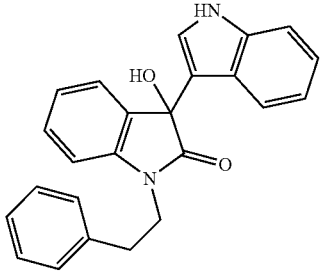

Chemical Formula 8

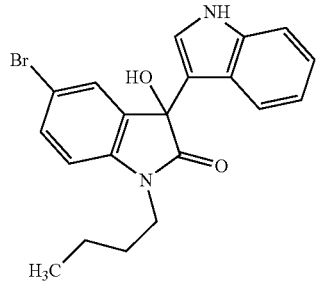

Chemical Formula 9

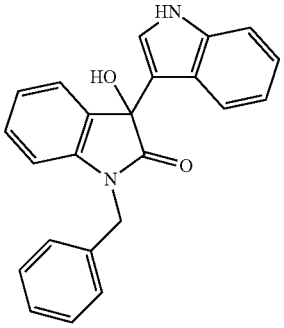

Chemcial Formula 10

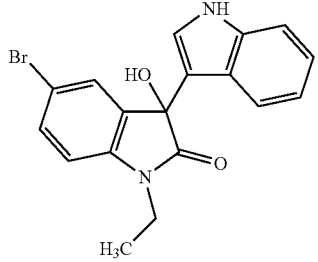

Chemcial Formula 11

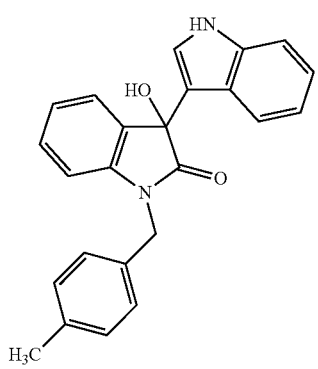

Chemcial Formula 12

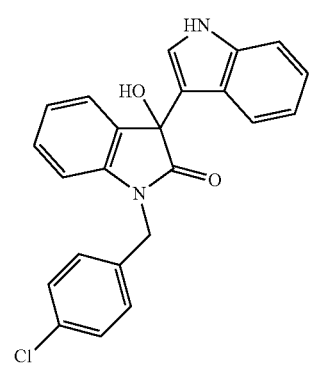

Chemcial Formula 13

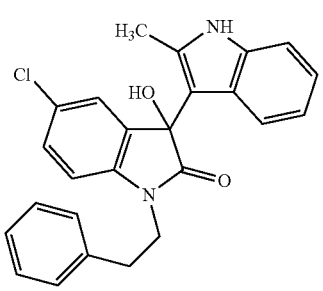

Chemcial Formula 14

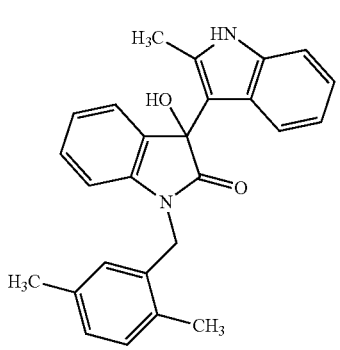

Chemcial Formula 15

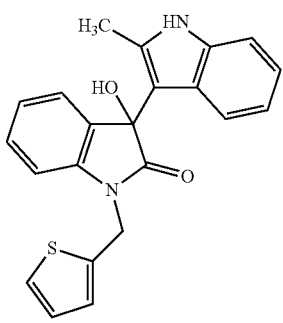

Chemcial Formula 16

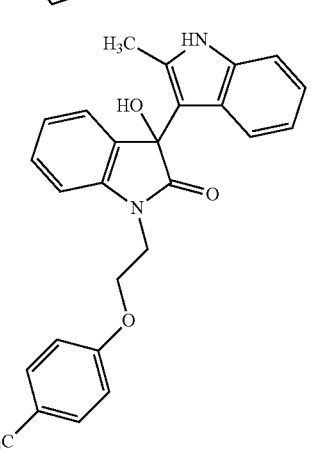

Chemical Formula 17

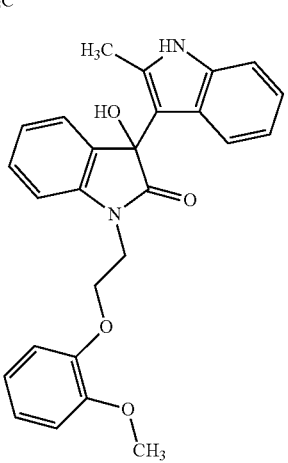

More specifically, the indole-3-carbinol derivative of the present disclosure represented by Chemical Formula 1 is selected from a group consisting of the compounds represented by Chemical Formulae 3 and 5-7.

Figure 1:
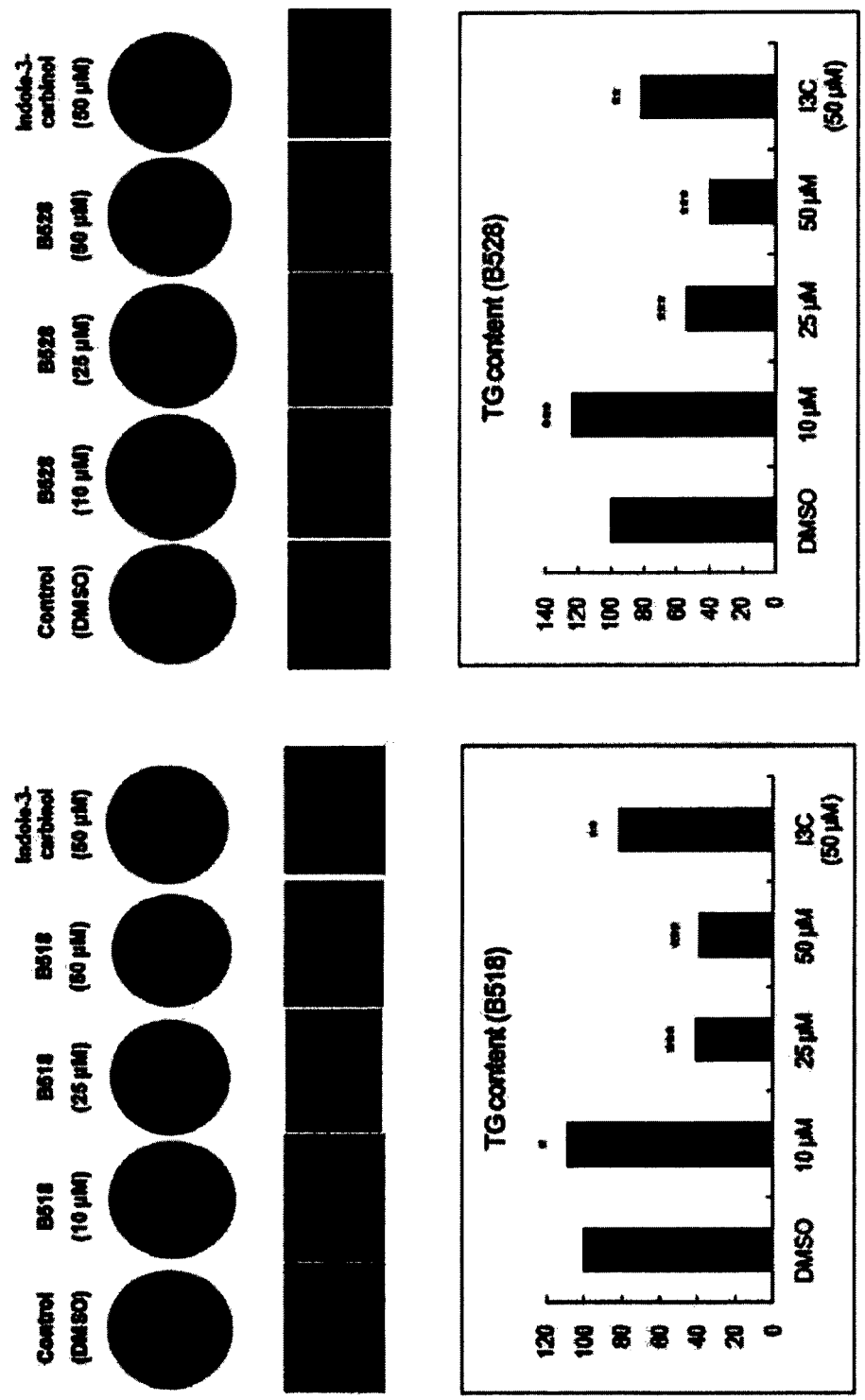
FIG. 1 shows a result of comparing preadipocyte differentiation inhibiting effect and intracellular triglyceride accumulation of indole-3-carbinol derivatives B518 and B528 with those of indole-3-carbinol. *,  and * respectively indicate significant difference with DMSO-treated control cells (*: P<0.05, : P<0.01 and *: P<0.001 in Student's t-test).
Figure 2:
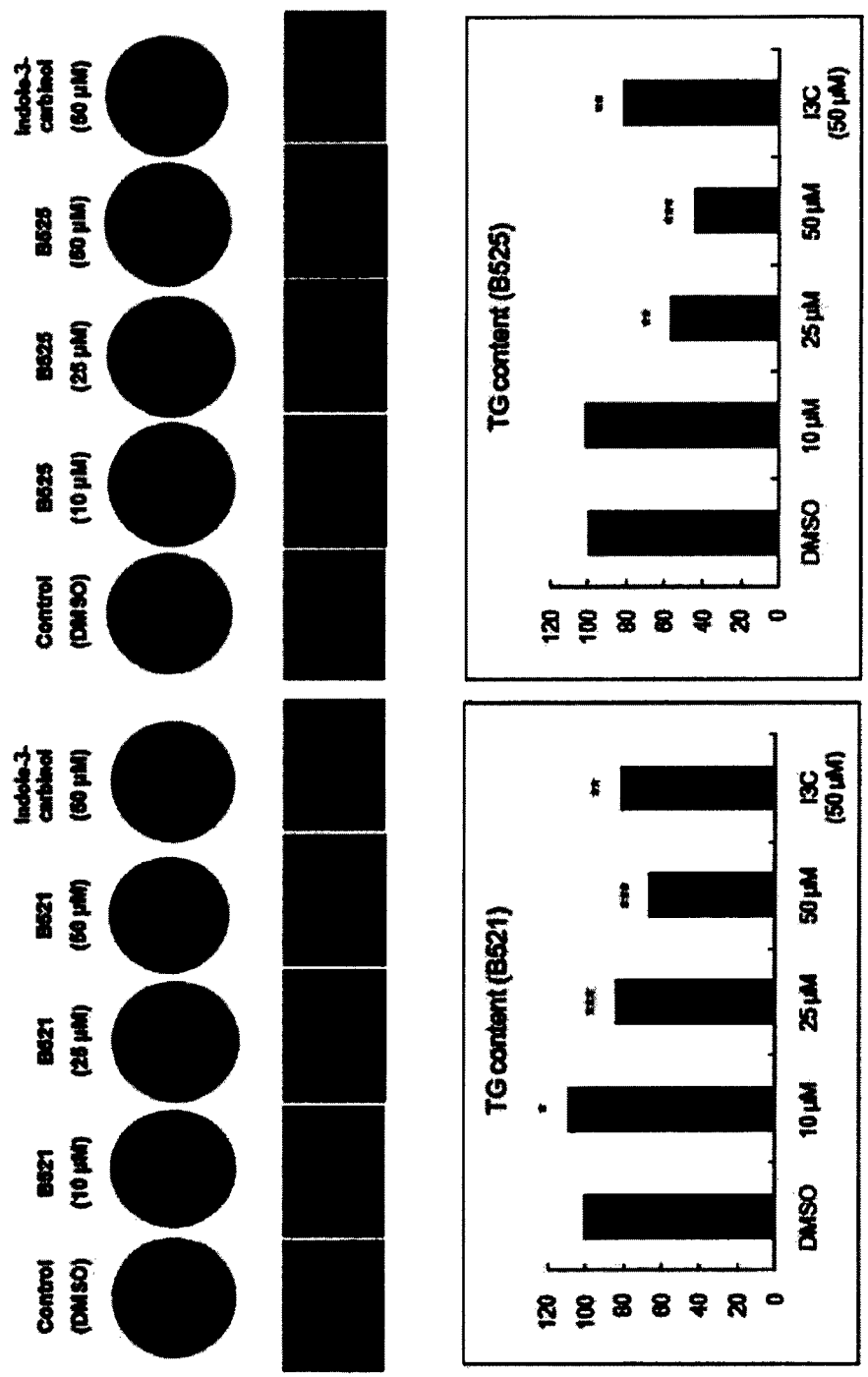
FIG. 2 shows a result of comparing preadipocyte differentiation inhibiting effect and intracellular triglyceride accumulation of indole-3-carbinol derivatives B521 and B525 with those of indole-3-carbinol. *,  and * respectively indicate significant difference with DMSO-treated control cells (*: P<0.05, : P<0.01 and *: P<0.001 in Student's t-test).
Figure 3:
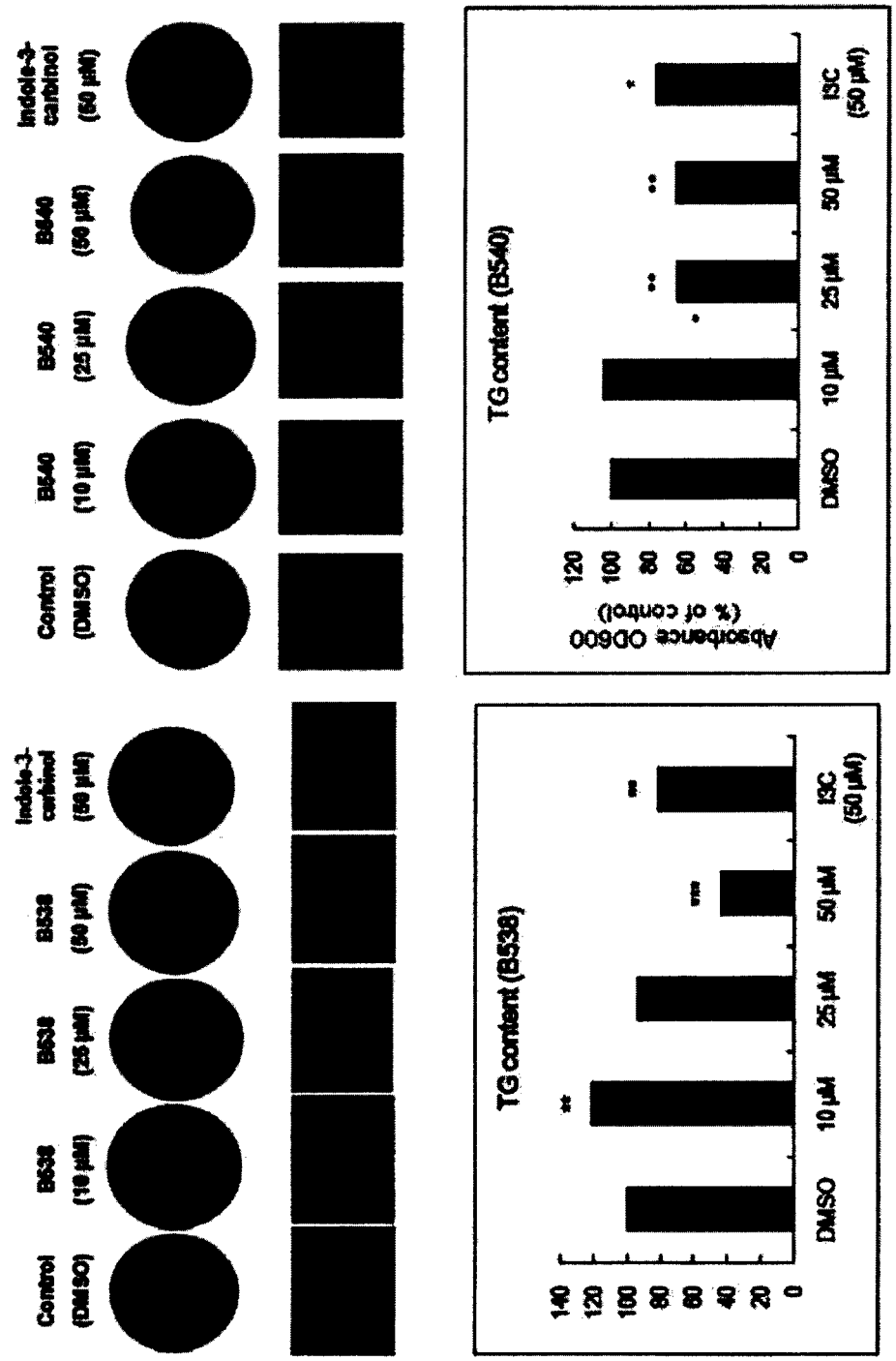
FIG. 3 shows a result of comparing preadipocyte differentiation inhibiting effect and intracellular triglyceride accumulation of indole-3-carbinol derivatives B538 and B540 with those of indole-3-carbinol. *,  and * respectively indicate significant difference with DMSO-treated control cells (*: P<0.05, : P<0.01 and *: P<0.001 in Student's t-test).
Figure 4:
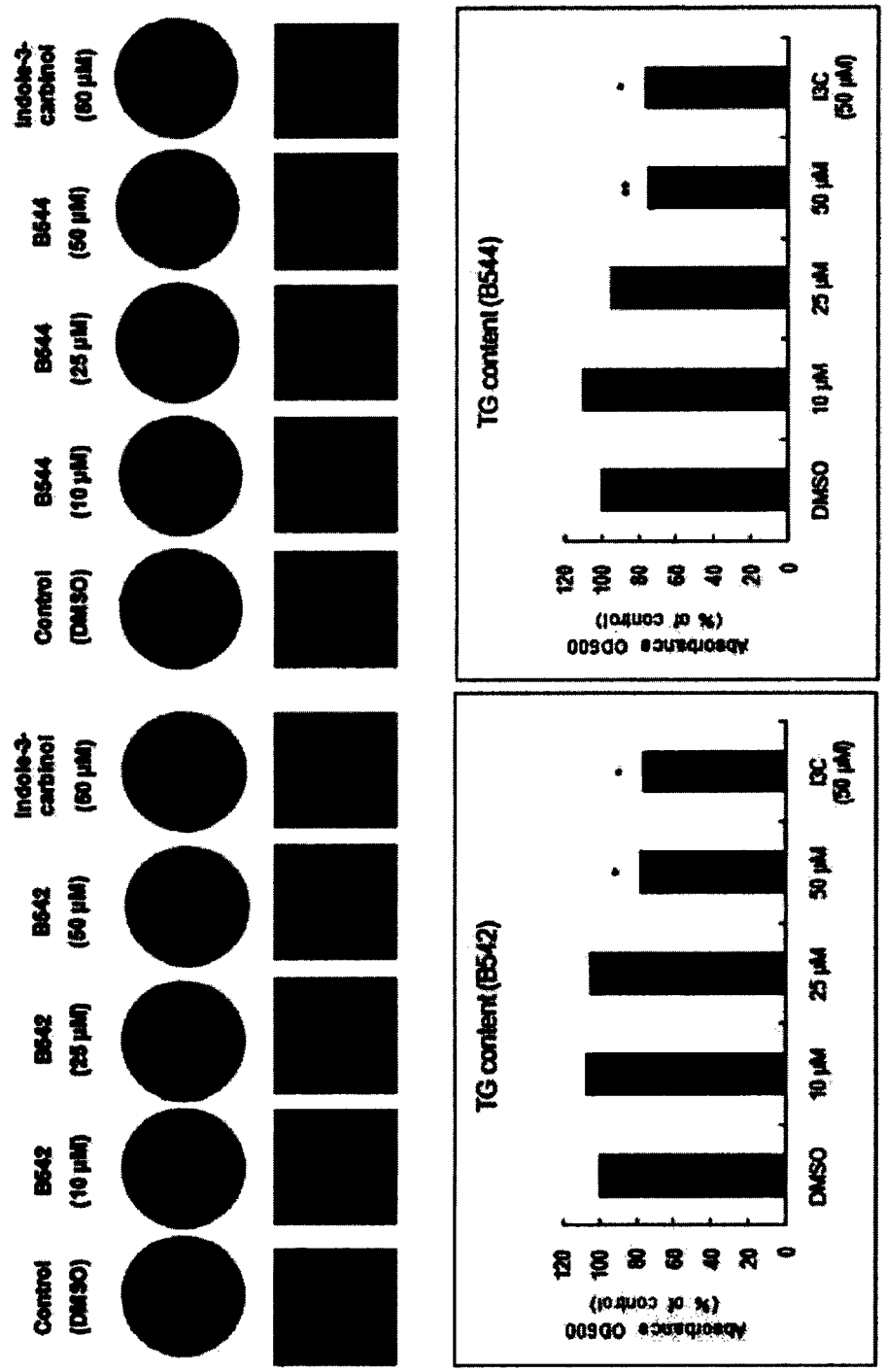
FIG. 4 shows a result of comparing preadipocyte differentiation inhibiting effect and intracellular triglyceride accumulation of indole-3-carbinol derivatives B542 and B544 with those of indole-3-carbinol. *,  and * respectively indicate significant difference with DMSO-treated control cells (*: P<0.05, : P<0.01 and *: P<0.001 in Student's t-test).
Figure 5:
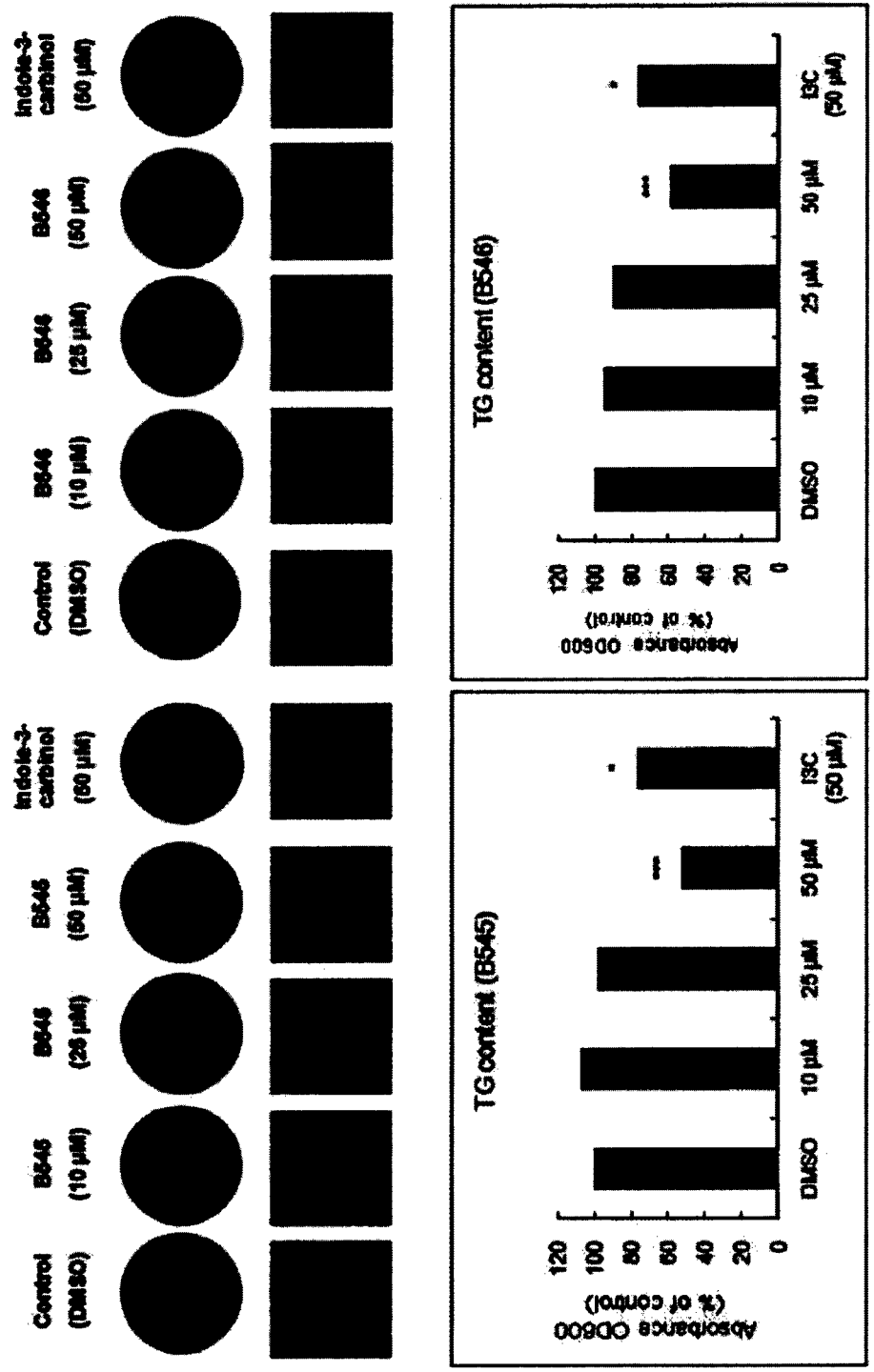
FIG. 5 shows a result of comparing preadipocyte differentiation inhibiting effect and intracellular triglyceride accumulation of indole-3-carbinol derivatives B545 and B546 with those of indole-3-carbinol. *,  and * respectively indicate significant difference with DMSO-treated control cells (*: P<0.05, : P<0.01 and *: P<0.001 in Student's t-test).
Figure 6:
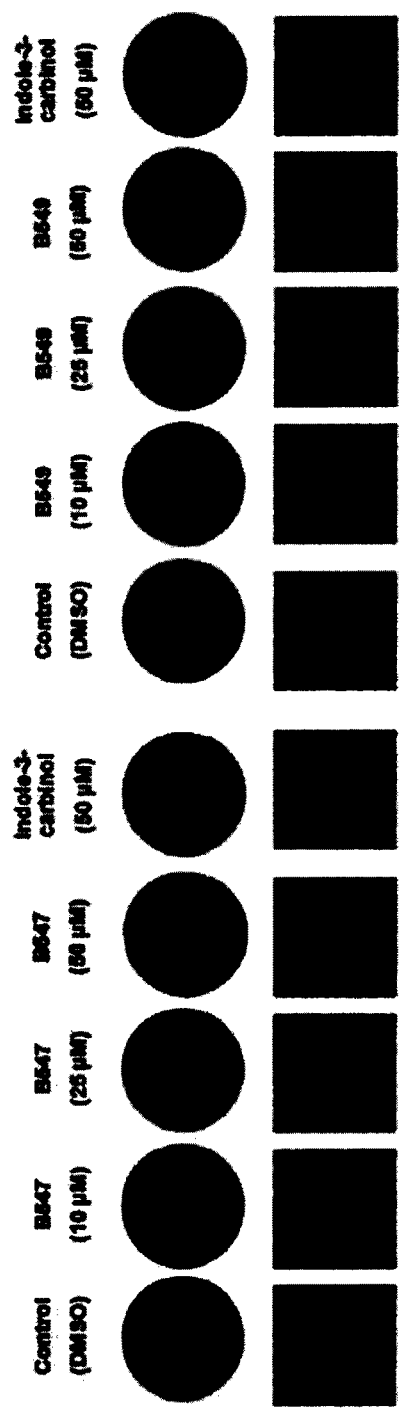
FIG. 6 shows a result of comparing preadipocyte differentiation inhibiting effect and intracellular triglyceride accumulation of indole-3-carbinol derivatives B547 and B549 with those of indole-3-carbinol. *,  and * respectively indicate significant difference with DMSO-treated control cells (*: P<0.05, : P<0.01 and *: P<0.001 in Student's t-test).
Figure 6:
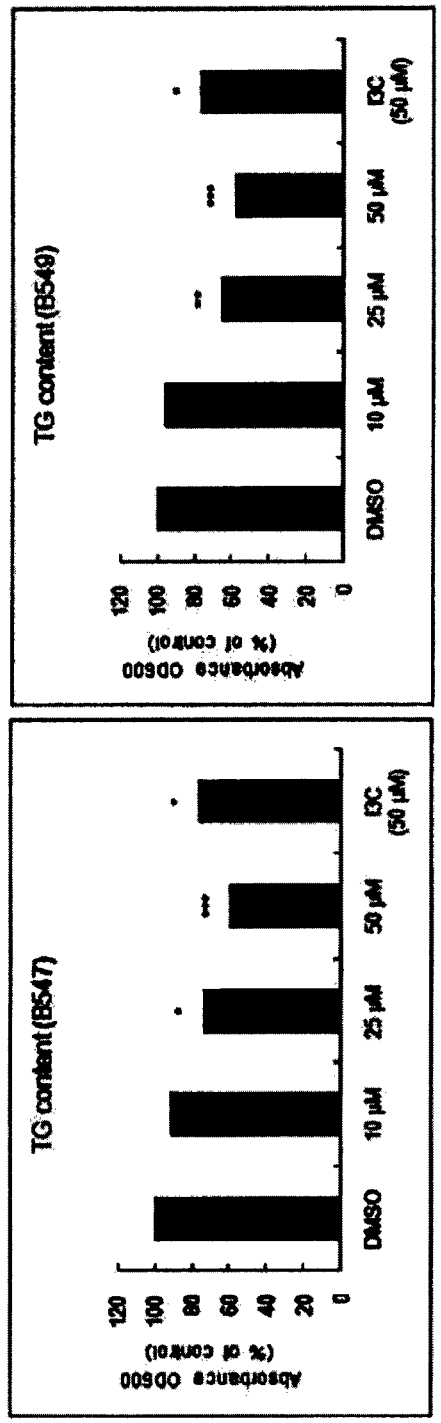
Figure 7:
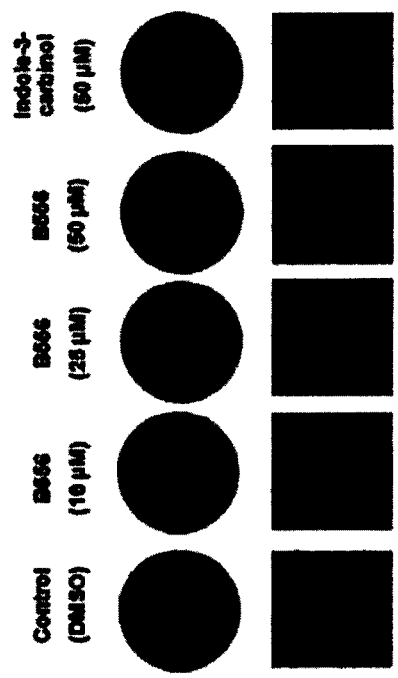
FIG. 7 shows a result of comparing preadipocyte differentiation inhibiting effect and intracellular triglyceride accumulation of indole-3-carbinol derivatives B551 and B556 with those of indole-3-carbinol. *,  and * respectively indicate significant difference with DMSO-treated control cells (*: P<0.05, : P<0.01 and *: P<0.001 in Student's t-test).
Figure 7:
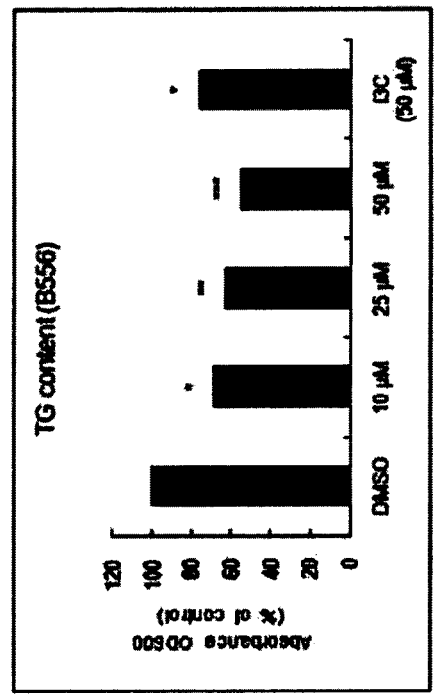
Figure 7:
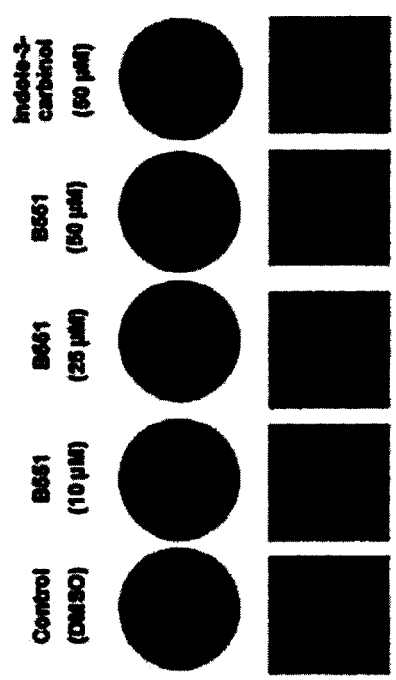
Figure 7:
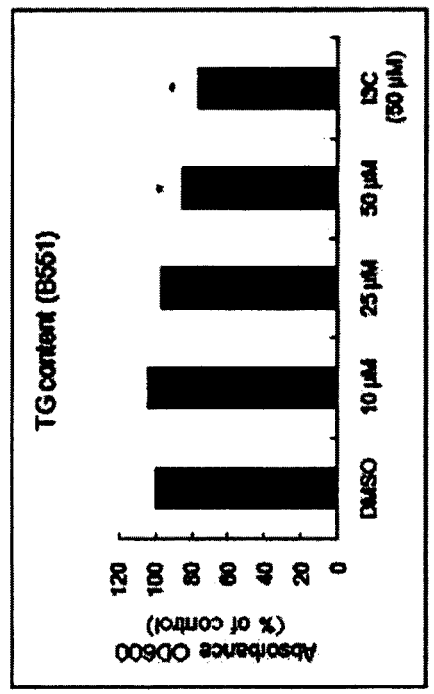
Figure 8:
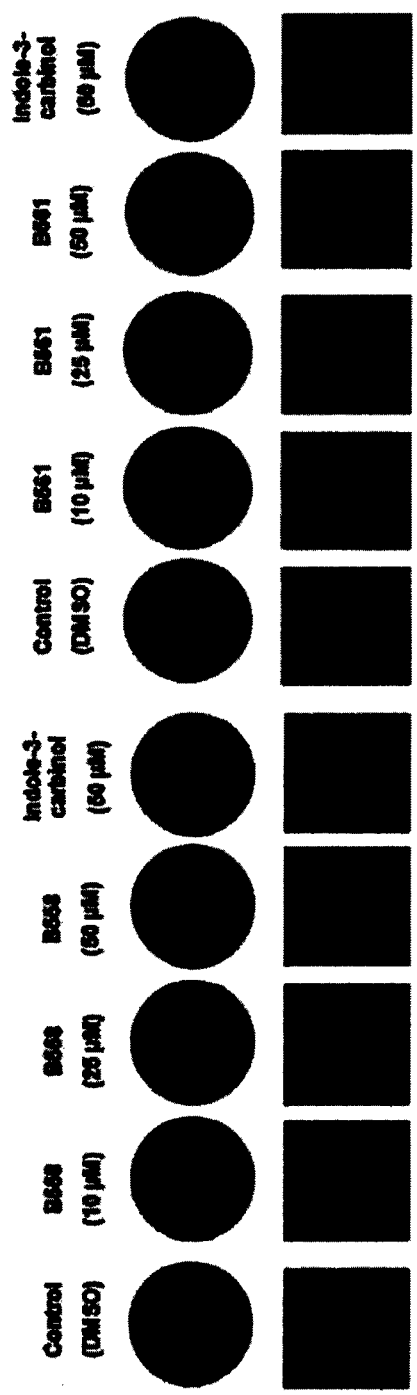
FIG. 8 shows a result of comparing preadipocyte differentiation inhibiting effect and intracellular triglyceride accumulation of indole-3-carbinol derivatives B558 and B561 with those of indole-3-carbinol. *,  and * respectively indicate significant difference with DMSO-treated control cells (*: P<0.05, : P<0.01 and *: P<0.001 in Student's t-test).
Figure 8:
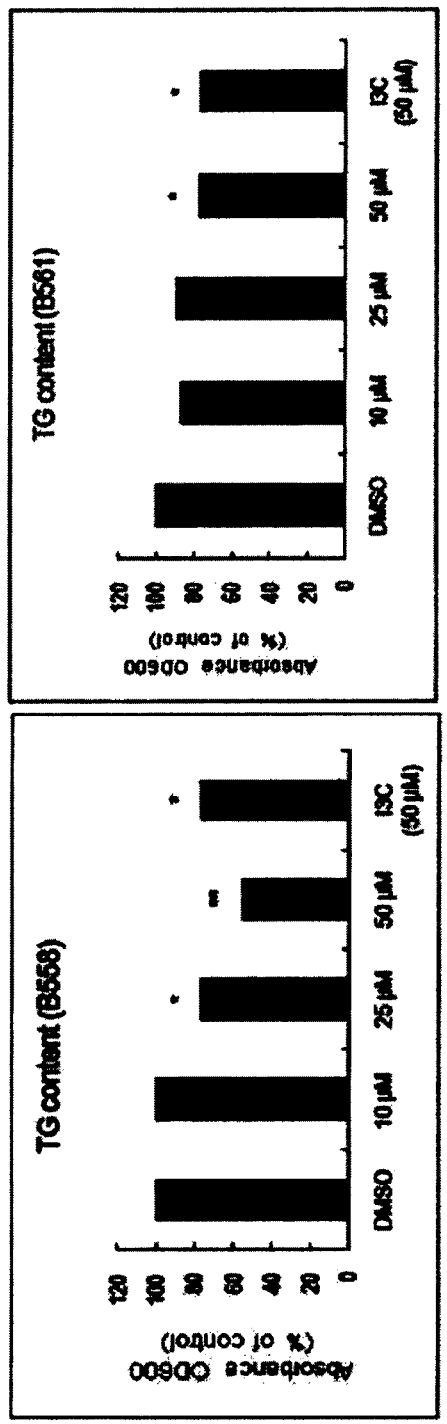

The 4 compounds, which are indole-3-carbinol derivatives B518, B525, B528 and B538 (Table 1), effectively reduce triglyceride accumulation in cells (see FIGS. 1-3).

In an exemplary embodiment of the present disclosure, the indole-3-carbinol derivative of the present disclosure represented by Chemical Formula 2 is a compound represented by Chemical Formula 18:

Chemical Formula 18

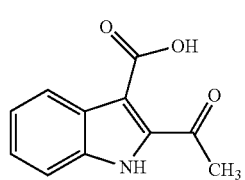

When the composition of the present disclosure is prepared as a pharmaceutical composition, the pharmaceutical composition of the present disclosure may comprise a pharmaceutically acceptable excipient. The pharmaceutically acceptable excipient included in the pharmaceutical composition of the present disclosure is one commonly used in the preparation of formulations and includes lactose, dextrose, sucrose, sorbitol, mannitol, starch, gum acacia, calcium phosphate, alginate, gelatin, calcium silicate, microcrystalline cellulose, polyvinylpyrrolidone, cellulose, water, syrup, methyl cellulose, methyl hydroxybenzoate, propyl hydroxybenzoate, talc, magnesium stearate, mineral oil, etc., but is not limited thereto. The pharmaceutical composition of the present disclosure may further include, in addition to the above-described components, a lubricant, a wetting agent, a sweetener, a fragrance, an emulsifier, a suspending agent, a preservative, or the like. Suitable pharmaceutically acceptable excipients and formulations are described in detail in *Remington's Pharmaceutical Sciences* (19th ed., 1995).

The pharmaceutical composition of the present disclosure may be administered orally or parenterally. When administered parenterally, it may be administered intravenously, subcutaneously, intramuscularly, intraabdominally, transdermally, or the like.

An appropriate administration dosage of the pharmaceutical composition of the present disclosure may be determined variously depending on such factors as preparation method, administration method, age, body weight and gender of a patient, pathological condition, diet, administration time, administration route, excretion rate or response sensitivity. Specifically, a daily dosage of the pharmaceutical composition of the present disclosure may be 0.001-100 mg/kg.

The pharmaceutical composition of the present disclosure may be prepared into a unit dosage form or multiple dosage form along with a pharmaceutically acceptable excipient and/or carrier according to a method that can be easily employed by those skilled in the art. The formulation may be in the form of solution in oily or aqueous medium, suspension, syrup, emulsion, extract, dust, powder, granule, tablet or capsule, and may further include a dispersant or stabilizer.

The present disclosure provides a food composition for preventing or improving obesity, hyperlipidemia, fatty liver or diabetes, comprising the indole-3-carbinol derivative of the present disclosure as an active ingredient. A description about the indole-3-carbinol derivative will be omitted to avoid unnecessary redundancy.

When the composition of the present disclosure is prepared as a food composition, the pharmaceutical composition of the present disclosure may comprise, in addition to the indole-3-carbinol derivative of the present disclosure as the active ingredient, ingredients commonly added for preparation of food. For example, proteins, carbohydrates, fats, nutrients, seasoning or flavors may be added. The carbohydrate may be, for example, a sugar such as a monosaccharide, e.g. glucose, fructose, etc., a disaccharide, e.g. maltose, sucrose, oligosaccharide, etc. or a polysaccharide, e.g. dextrin, cyclodextrin, etc. or a sugar alcohol such as xylitol, sorbitol, erythritol, etc. The flavor may be a natural flavor [thaumatin, stevia extract (e.g. rebaudioside A, glycyrrhizin, etc.]) or a synthetic flavor (saccharin, aspartame, etc.).

For example, when the food composition of the present disclosure is prepared as a drink, it may further comprise, in addition to the indole-3-carbinol derivative of the present disclosure as the active ingredient, citric acid, high-fructose corn syrup, sugar, glucose, acetic acid, malic acid, fruit juice, eucommia extract, jujube extract, licorice extract, or the like.

Mode For Invention

The examples and experiments will now be described. The following examples and experiments are for illustrative purposes only and not intended to limit the scope of the present disclosure.

Materials and Methods

Cell Culturing and Treatment with Indole-3-Carbinol Derivative Compounds

Mouse adipocyte cell line (3T3-L1) was used to investigate the effect of various indole-3-carbinol derivatives on differentiation and growth of adipocytes. The preadipocytes, 3T3-L1 cells, were seeded on a 12-well plate and cultured to confluency using Dulbecco's modified Eagle's medium (DMEM) containing 1% penicillin-streptomycin, 1% nonessential amino acid and 10% fatal bovine serum (FBS), in a 5% $CO_2$ incubator at 37° C. The 3T3-L1 cells grown to confluency were cultured for 2 days in MDI medium containing 0.5 mM isobutylmethylxanthine, 1 μM dexamethasone and 1 μg/mL insulin to differentiate them into adipocytes. Then, the cells were further cultivated in DMEM containing 1 μg/mL insulin to differentiate them into mature adipocytes. The cells were further cultured for 10 more days while replacing DMEM every other day to obtain fully differentiated adipocytes.

From the first day when MDI was added to the 3T3-L1 cells, 16 indole-3-carbinol derivative compounds were treated at concentrations of 0.1, 1, 10, 50 and 100 μM with 2-day intervals. The structure and molecular weight of the 16 indole-3-carbinol derivatives (B518, B521, B525, B528, B538, B540, B542, B544, B545, B546, B547, B549, B551, B556, B558 and B561) are described in Table 1. The derivative compounds were used after being dissolved in DMSO. Only DMSO was added to the negative control group.

TABLE 1

Structure and molecular weight of indole-3-carbinol derivatives

| Derivatives | Chemical name | Structure | Molecular weight |
|---|---|---|---|
| B518 | 5'-Bromo-3'-hydroxy-1'-(2-phenylethyl)-1',3'-dihydro-1H,2'H-3,3'-biindol-2'-one | 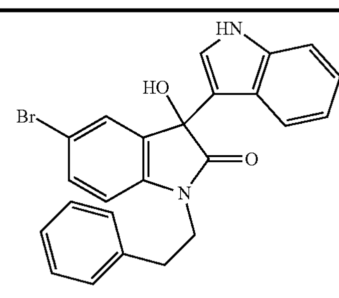 | 447.34 |

TABLE 1-continued

Structure and molecular weight of indole-3-carbinol derivatives

| Derivatives | Chemical name | Structure | Molecular weight |
|---|---|---|---|
| B521 | 5'-Chloro-3'-hydroxy-1'-methyl-1',3'-dihydro-1H,2'H-3,3'-biindol-2'-one | 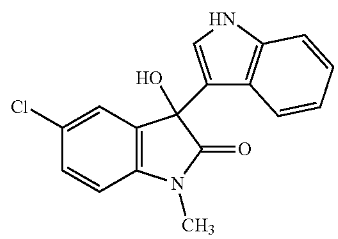 [SMILES: CN1C(=O)C(O)(c2c[nH]c3ccccc23)c2cc(Cl)ccc21] | 312.76 |
| B525 | 1'-Allyl-5'-bromo-3'-hydroxy-2-methyl-1',3'-dihydro-1H,2'H-3,3'-biindol-2'-one | 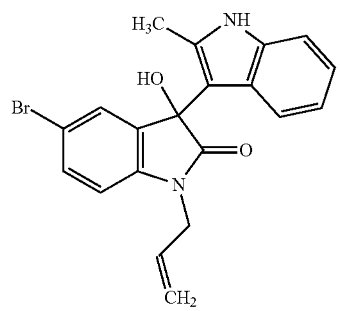 [SMILES: C=CCN1C(=O)C(O)(c2c(C)[nH]c3ccccc23)c2cc(Br)ccc21] | 397.27 |
| B528 | 5'-Bromo-1'-ethyl-3'-hydroxy-2-methyl-1',3'-dihydro-1H,2'H-3,3'-biindol-2'-one | 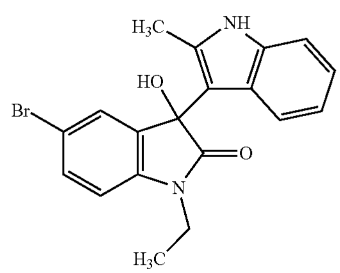 [SMILES: CCN1C(=O)C(O)(c2c(C)[nH]c3ccccc23)c2cc(Br)ccc21] | 385.26 |
| B538 | 3'-Hydroxy-1'-(2-phenylethyl)-1',3'-dihydro-1H,2'H-3,3'-biindol-2'-one | 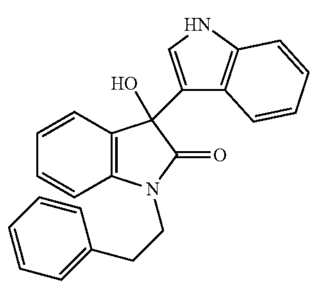 [SMILES: O=C1N(CCc2ccccc2)c2ccccc2C1(O)c1c[nH]c2ccccc12] | 368.44 |
| B540 | 5'-Bromo-1'-butyl-3'-hydroxy-1',3'-dihydro-1H,2'H-3,3'-biindol-2'-one | 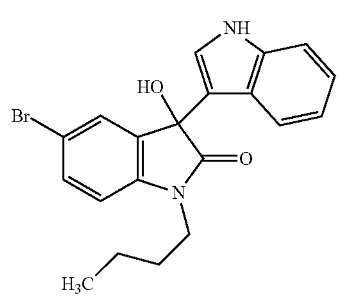 [SMILES: CCCCN1C(=O)C(O)(c2c[nH]c3ccccc23)c2cc(Br)ccc21] | 399.29 |

TABLE 1-continued

Structure and molecular weight of indole-3-carbinol derivatives

| Derivatives | Chemical name | Structure | Molecular weight |
|---|---|---|---|
| B542 | 1'-Benzyl-3'-hydroxy-1',3'-dihydro-1H,2'H-3,3'-biindol-2'-one | 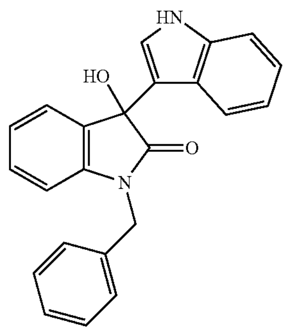 [SMILES: O=C1N(Cc2ccccc2)c2ccccc2C1(O)c1c[nH]c2ccccc12] | 354.41 |
| B544 | 5'-Bromo-1'-ethyl-3'-hydroxy-1',3'-dihydro-1H,2'H-3,3'-biindol-2'-one | 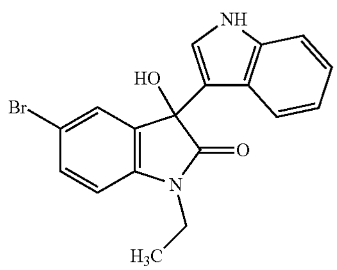 [SMILES: CCN1C(=O)C(O)(c2c[nH]c3ccccc23)c2cc(Br)ccc21] | 371.24 |
| B545 | 3'-Hydroxy-1'-(4-methylbenzyl)-1',3'-dihydro-1H,2'H-3,3'-biindol-2'-one | 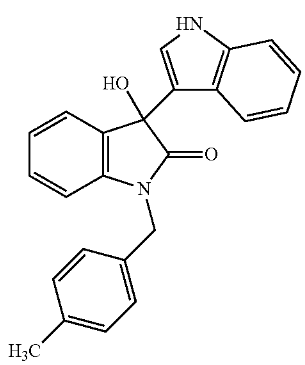 [SMILES: Cc1ccc(CN2C(=O)C(O)(c3c[nH]c4ccccc34)c3ccccc32)cc1] | 368.44 |
| B546 | 1'-(4-Chlorobenzyl)-3'-hydroxy-1',3'-dihydro-1H,2'H-3,3'-biindol-2'-one | 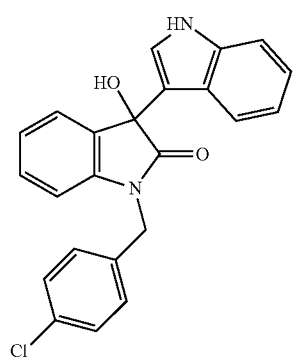 [SMILES: O=C1N(Cc2ccc(Cl)cc2)c2ccccc2C1(O)c1c[nH]c2ccccc12] | 388.86 |

TABLE 1-continued

Structure and molecular weight of indole-3-carbinol derivatives

| Derivatives | Chemical name | Structure | Molecular weight |
|---|---|---|---|
| B547 | 5'-Chloro-3'-hydroxy-2-methyl-1'-(2-phenylethyl)-1',3'-dihydro-1H,2'H-3,3'-biindol-2'-one | 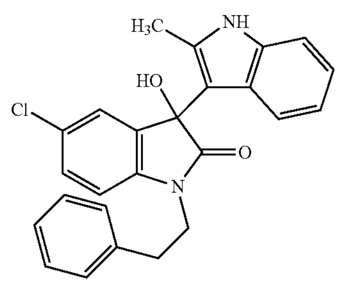 [SMILES: Cc1[nH]c2ccccc2c1C1(O)C(=O)N(CCc2ccccc2)c2ccc(Cl)cc21] | 416.91 |
| B549 | 1'-(2,5-Dimethylbenzyl)-3'-hydroxy-2-methyl-1',3'-dihydro-1H,2'H-3,3'-biindol-2'-one | 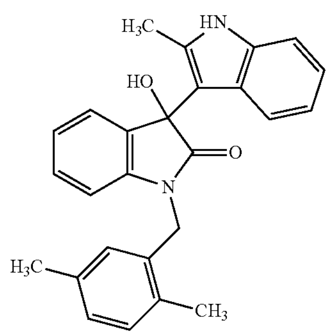 [SMILES: Cc1ccc(C)c(CN2C(=O)C(O)(c3c(C)[nH]c4ccccc34)c3ccccc32)c1] | 396.49 |
| B551 | 3'-Hydroxy-2-methyl-1'-(2-thienylmethyl)-1',3'-dihydro-1H,2'H-3,3'-biindol-2'-one | 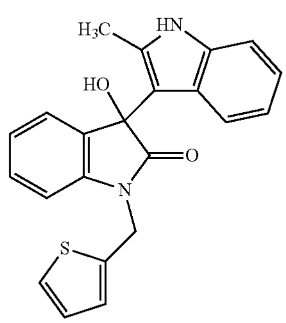 [SMILES: Cc1[nH]c2ccccc2c1C1(O)C(=O)N(Cc2cccs2)c2ccccc21] | 374.46 |
| B556 | 3'-Hydroxy-2-methyl-1'-[2-(4-methylphenoxy)ethyl]-1',3'-dihydro-1H,2'H-3,3'-biindol-2'-one | 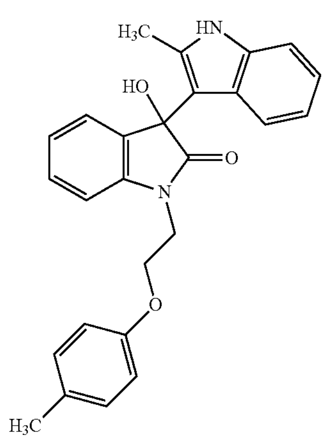 [SMILES: Cc1ccc(OCCN2C(=O)C(O)(c3c(C)[nH]c4ccccc34)c3ccccc32)cc1] | 412.49 |

TABLE 1-continued

Structure and molecular weight of indole-3-carbinol derivatives

| Derivatives | Chemical name | Structure | Molecular weight |
|---|---|---|---|
| B558 | 3'-Hydroxy-1'-[2-(2-methoxyphenoxy)ethyl]-2-methyl-1',3'-dihydro-1H,2'H-3,3'-biindol-2'-one | 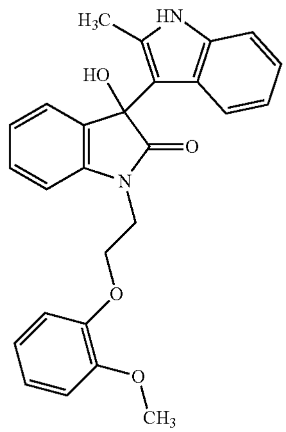 [SMILES: COc1ccccc1OCCN1C(=O)C(O)(c2c(C)[nH]c3ccccc23)c2ccccc21] | 428.49 |
| B561 | 2-Acetyl-1H-indole-3-carboxylic acid | 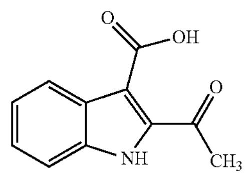 | 203.2 |

Oil Red O Staining

After culturing for a total of 14 days, the medium was removed when the differentiation was completed and lipid droplets in the differentiated adipocytes were stained. For this, the cells were washed twice with phosphate buffered saline (PBS), fixed in 10% buffered neutral formalin (BNF) for 1 hour, washed once again with PBS, stained for 1 hour by adding 1 mL of Oil Red O dye, which specifically stains fat red, on the 12-well plate, and washed twice with distilled water. In order to measure the level of triglyceride contained in the differentiated 3T3-L1 cells, the stained lipid droplets were dissolved in 1 mL of isobutanol and optical density (OD) value was measured at 600 nm.

Preparation of Test Diet and Breeding of Test Animals

The obesity-inducing control diet used in the test was high-fat diet (HFD: 40% fat calorie, 17 g lard+3% corn oil/100 g diet). Diets supplemented with indole-3-carbinol derivatives (B525 and B528) had the same composition as HFD, except that each derivative was included at 0.05% (see Table 2). The diabetic drug metformin was added at 0.1% or the hyperlipidemic drug atorvastatin was added at 0.01% to HFD as controls. The normal diet group (Chow) was fed with commercially available rodent chow.

TABLE 2

Composition of test diets

| Ingredients | High-fat diet (HFD) | B525-supplemented diet (B525) | B528-supplemented diet (B528) | Atorvastatin-supplemented diet (Ator) | Metformin-supplemented diet (Metf) |
|---|---|---|---|---|---|
| Casein | 200 | 200 | 200 | 200 | 200 |
| D/L-Methionine | 3 | 3 | 3 | 3 | 3 |
| Corn starch | 111 | 110.5 | 110.5 | 110 | 110.9 |
| Sucrose | 370 | 370 | 370 | 370 | 370 |
| Cellulose | 50 | 50 | 50 | 50 | 50 |
| Corn oil | 30 | 30 | 30 | 30 | 30 |
| Lard | 170 | 170 | 170 | 170 | 170 |
| Vitamin complex | 12 | 12 | 12 | 12 | 12 |
| Mineral complex | 42 | 42 | 42 | 42 | 42 |
| Choline bitartrate | 2 | 2 | 2 | 2 | 2 |
| Cholesterol | 10 | 10 | 10 | 10 | 10 |
| Tert-butylhydroquinone | 0.04 | 0.04 | 0.04 | 0.04 | 0.04 |
| Test substance | — | 0.5 | 0.5 | 1 | 0.1 |
| Total (g) | 1,000 | 1000 | 1000 | 1000 | 1000 |
| Fat (% calorie) | 39.0 | 39.0 | 39.0 | 39.0 | 39.0 |
| Total calorie (kJ/kg diet) | 19,315 | 19315 | 19315 | 19315 | 19315 |

56 5-week-old male C57BL/6J mice (Orient, Korea) were accustomed to the laboratory environment for 1 week while feeding solid feed. Then, they were randomly divided into normal diet, high-fat diet and test groups (n=8/group) and bred for a total of 10 weeks. The diet was given between 10 and 11 a.m. every day together with water. Food intake was measured every day and body weight was measured once a week. In order to avoid transient body weight increase after feed intake, body weight was measured 2 hours after removing the feed. After fasting the test animal for at least 12 hours and anesthetizing with diethyl ether, blood, liver and visceral fat (epididymal fat, perirenal fat, mesenteric fat and retroperitoneal fat) were taken and weighed after washing with 0.1 M PBS (pH 7.4). Blood taken from the abdominal aorta was centrifuged at 1000×g for 15 minutes to separate the plasma.

Biochemical Analysis of Blood

After 10 weeks of breeding, total cholesterol, triglyceride and glucose levels in the plasma and lipid level in the liver tissue were measured as follows. Total cholesterol, triglyceride and free fatty acid levels in the plasma were measured twice for each using a commercially available kit (Bio Clinical System).

Oral Glucose Tolerance Test

On week 8 after feeding the test diet, oral glucose tolerance test was performed for all the groups. After fasting the mouse for 16 hours, glucose (2 g glucose/10 mL distilled water/kg body weight) was orally administered. Before and 15, 30, 60 and 120 minutes after the oral administration, the tail end was cut by about 1 cm and blood was taken. Glucose level was measured using a glucose meter.

Lipid Level in Liver Tissue

Lipids were extracted from the liver tissue according to Folch et al.'s method Folch J et al., *J Biol. Chem.* 226: 497-509 (1957)). After adding 1 mL of distilled water to 0.25 g of liver tissue, the liver tissue was homogenized using a Polytron homogenizer (IKA-Werke GmbH & Co., Ultra-Turrax, Staufen, Germany). After adding 5 mL of chloroform:methanol solution (2:1, v/v) to the homogenate and mixing well, the mixture was centrifuged at 1000×g for 10 minutes. After adding 2 mL of chloroform:methanol solution (2:1, v/v) again to the supernatant, the same procedure was repeated to completely separate the lipid components of the liver. After adding 3 mL of chloroform:methanol:0.05% $CaCl_2$ (3:48:47, v/v/v) solution to the remaining pellets and mixing well for 1 minute, followed by centrifugation at 1000×g for 10 minutes, the resulting pellets were completely dried with nitrogen gas. The dried lipids were dissolved in 1 mL of methanol and then analyzed.

The same kit (Bio Clinical System) as that used for the plasma analysis was used to measure the triglyceride and cholesterol levels of the liver tissue.

Test Result

Inhibition of Adipocyte Differentiation by Indole-3-Carbinol Derivatives

The 16 indole-3-carbinol derivatives (B518, B521, B525, B528, B538, B540, B542, 8544, B545, B546, 8547, B549, B551, B556, B558 and B561) reduced the differentiation of the preadipocytes 3T3L1 in a concentration-dependent manner (FIGS. 1-8). When the amount of the fats stained with Oil Red O was quantitated by spectrophotometry, the OD value also decreased in a concentration-dependent manner. For reference, inhibition of preadipocyte differentiation and intracellular triglyceride accumulation for the derivatives were compared with those for indole-3-carbinol.

Body Weight and Visceral Fat Decrease in Mouse by Indole-3-Carbinol Derivatives (B525 and B528)

Figure 9:
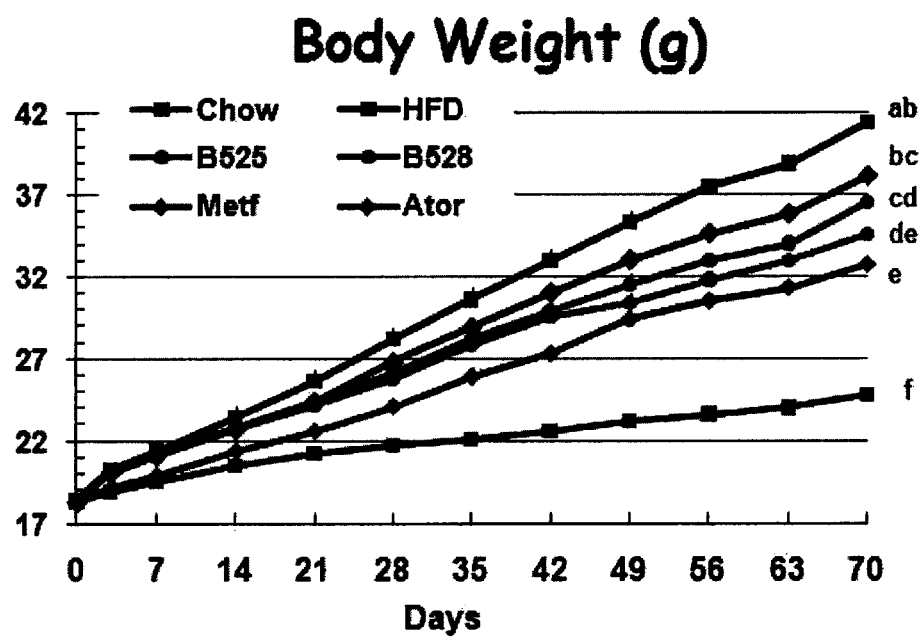
FIG. 9 shows body weight gain of mice fed with test diet. The result is represented as mean±SEM (standard error) of 8 mice. The characters above the bars indicate significant difference by one-way analysis of variance (ANOVA) test (P<0.001).
Figure 9:
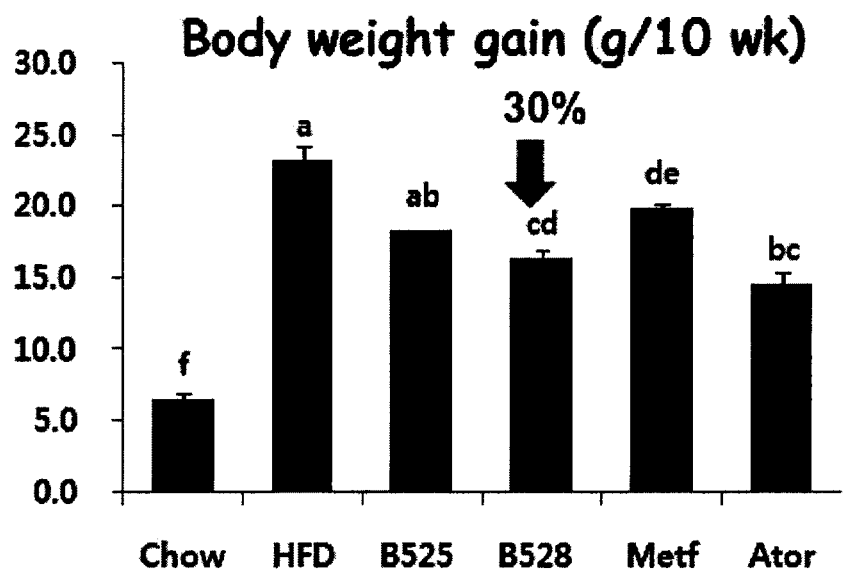

After feeding the test diet for 10 weeks, the B525- and B528-supplemented groups showed significant decrease of body weight gain by 21% and 30%, respectively, as compared to HFD. The body weight reducing effect of the indole-3-carbinol derivatives was comparable or better as compared to the controls metformin or atorvastatin (FIG. 9).

FIG. 10 shows images of the mice after feeding the test diet for 10 weeks. It can be seen that the visceral fat was significantly reduced for the B525 and B528 groups as compared to HFD. The B525 group showed significantly reduced weight of epididymal fat, perirenal fat, mesenteric fat and retroperitoneal fat as compared to HFD. The total visceral fat weight was significantly reduced by 20%. Also, the B528 group showed significantly reduced weight of epididymal fat, perirenal fat, mesenteric fat and retroperitoneal fat as compared to HFD. The total visceral fat weight was significantly reduced by 26% (FIG. 10). Accordingly, it was confirmed that B528 and B525 have excellent effect of reducing body weight and visceral fat.

Effect of Preventing and Treating Hyperlipidemia in Mouse by Indole-3-Carbinol Derivatives (B525 and B528)

After feeding the test diet for 10 weeks, the B525 group showed significantly reduced triglyceride level (32%), total cholesterol level (18%) and arteriosclerotic index (30%) in blood plasma as compared to HFD. And, the B528 group showed significantly reduced triglyceride level (38%), total cholesterol level (21%) and arteriosclerotic index (35%) in blood plasma as compared to HFD. There was no significant difference in blood HDL cholesterol level in HFD and all the test groups (FIG. 11). Accordingly, it was confirmed that B528 and B525 have excellent effect of improving hyperlipidemia induced with high-fat diet.

Effect of Preventing and Treating Type 2 Diabetes in Mouse by Indole-3-Carbinol Derivatives (B525 and B528)

After feeding B525 and B528 for 8 weeks to the mice feeding high-fat diet, fasting blood sugar level was significantly reduced by 37% and 39%, respectively, as compared to HFD. Accordingly, it was confirmed that B528 and B525 have the effect of improving fasting blood sugar level increase induced with high-fat diet.

When blood glucose level was measured after orally administering glucose (2 g glucose/10 mL distilled water/kg body weight) to the mouse and taking blood 15, 30, 60 and 120 minutes later from the tail vein, the B528 group showed decreased blood glucose level at all times as compared to HFD. In particular, statistically significant decrease of blood glucose level (−29%) was observed after 60 minutes (FIG. 12). The area under the curve (AUC) of the blood glucose level decreased significantly for the B528 group as compared to HFD. Accordingly, it was confirmed that B528 and B525 have excellent effect of improving oral glucose tolerance, better than the controls metformin and atorvastatin (FIG. 12).

Effect of Preventing and Treating Non-Alcoholic Fatty Liver in Mouse by Indole-3-Carbinol Derivatives (B525 and B528)

FIG. 13 shows images of mouse liver tissue after feeding the test diet for 10 weeks. It can be seen that HFD exhibits larger and brighter liver tissue as compared to Chow. The mice fed with B525 or B528 show smaller and darker liver tissue as compared to HFD, suggesting that fatty liver was improved. The liver weight of mouse was significantly decreased for the B525 and B528 groups, respectively by 26% and 31%, as compared to HFD (FIG. 13).

The B525 group showed significantly decreased triglyceride level (18%) and cholesterol level (22%) in liver tissue as compared to HFD, and the B528 group showed significantly decreased triglyceride level (34%) and cholesterol level (28%) in liver tissue as compared to HFD (FIG. 14). Accordingly, it was confirmed that B525 and B528 compound have the excellent effect of significantly improving fatty liver induced with high-fat diet.

Those skilled in the art will appreciate that the conceptions and specific embodiments disclosed in the foregoing description may be readily utilized as a basis for modifying or designing other embodiments for carrying out the same purposes of the present disclosure. Those skilled in the art will also appreciate that such equivalent embodiments do not depart from the spirit and scope of the disclosure as set forth in the appended claims.

The invention claimed is:

1. A method for treating obesity, dyslipidemia, fatty liver or diabetes, comprising administering to a subject in need thereof a therapeutically effective amount of a composition comprising an indole-3-carbinol derivative represented by Chemical Formula 1 as an active ingredient:

Chemical Formula 1

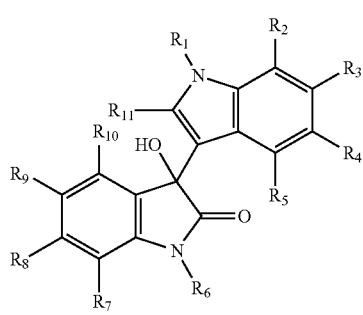

wherein $R_1$ is hydrogen or $C_1$-$C_4$ alkyl, $R_2$-$R_5$ are hydrogen, $R_7$-$R_{10}$ are independently hydrogen or halo, $R_6$ is $C_1$-$C_4$ alkyl, $C_2$-$C_6$ alkenyl, phenyl $C_1$-$C_4$ alkyl, 5- or 6-membered heteroaryl $C_1$-$C_4$ alkyl, phenoxy $C_1$-$C_4$ alkyl or $C_1$-$C_4$ alkoxyphenoxy $C_1$-$C_4$ alkyl, and $R_{11}$ is hydrogen or methyl.

2. The method according to claim 1, wherein $R_1$ in Chemical Formula 1 is hydrogen.

3. The method according to claim 1, wherein $R_7$-$R_{10}$ in Chemical Formula 1 are independently hydrogen, chlorine or bromine.

4. The method according to claim 1, wherein the heteroaryl of $R_6$ in Chemical Formula 1 is thiophene, furan, pyrrole or pyridine.

5. The method according to claim 4, wherein the heteroaryl is thiophene.

6. A method for treating obesity, dtyslipidemia, fatty liver or diabetes, comprising administering to a subject in need thereof a therapeutically effective amount of a composition comprising and indole-3-carbinol derivative represented be Chemical Formulas 3-17 as an active agent:

Chemical Formula 3

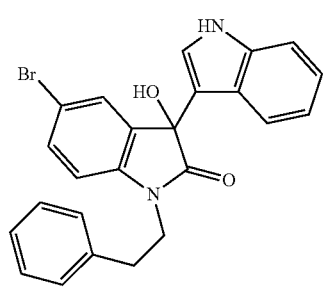

Chemical Formula 4

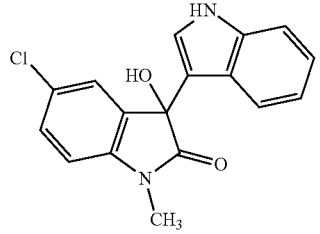

Chemical Formula 5

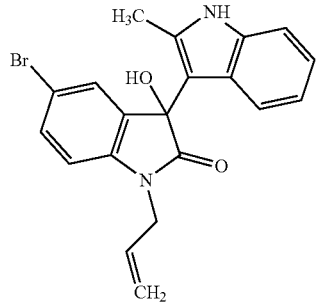

Chemical Formula 6

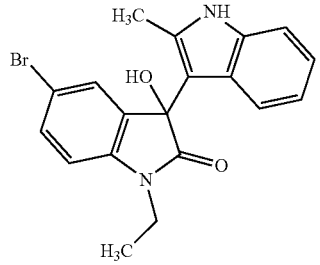

Chemical Formula 7

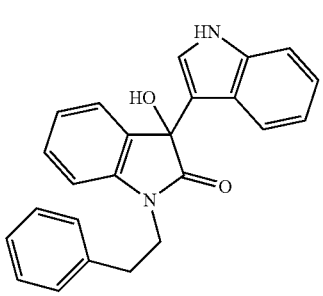

Chemical Formula 8

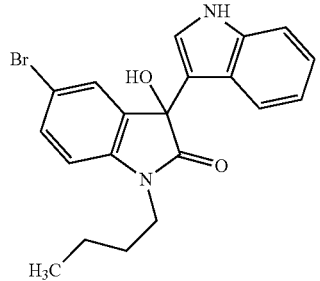

Chemical Formula 9
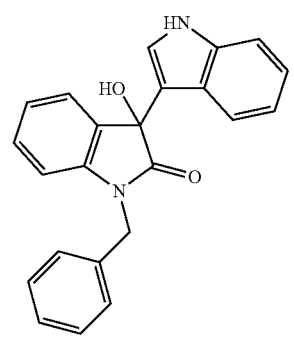
Chemical Formula 10
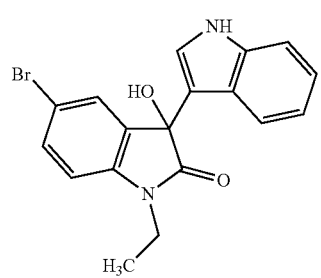
Chemical Formula 11
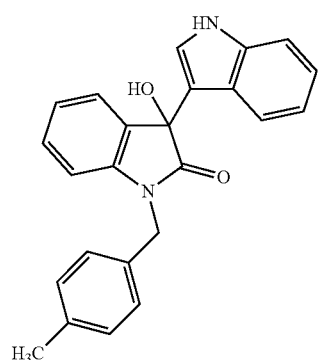
Chemical Formula 12
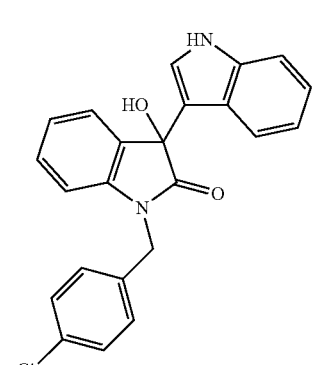
Chemical Formula 13
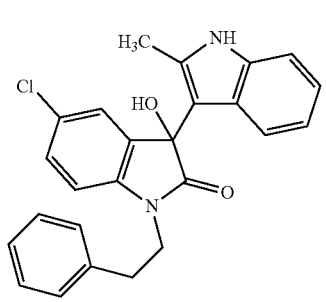
Chemical Formula 14
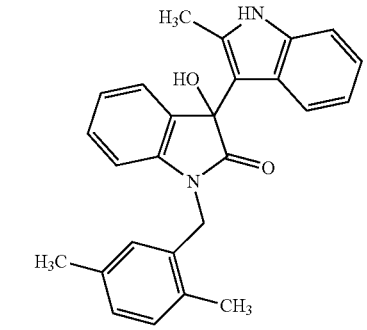
Chemical Formula 15
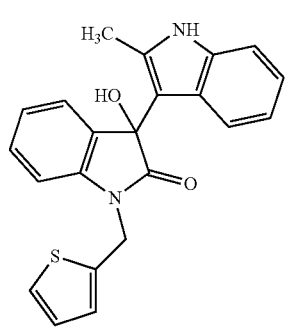
Chemical Formula 16
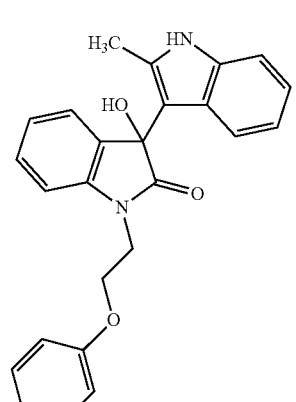
Chemical Formula 17
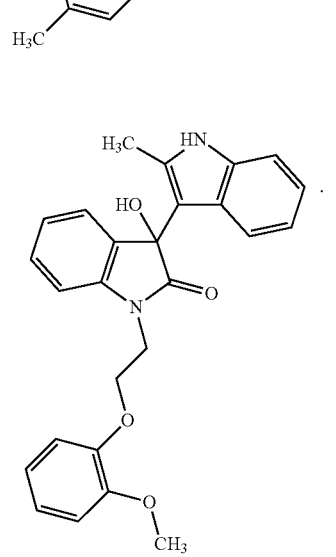

7. The method according to claim 6, wherein the indole-3-carbinol derivative represented by Chemical Formula 1 is selected from the group consisting of the compounds represented by Chemical Formulas 3 and 5-7.

* * * * *